(12) United States Patent
Taniguchi et al.

(10) Patent No.: US 6,673,799 B1
(45) Date of Patent: Jan. 6, 2004

(54) CYANOPHENYL DERIVATIVE

(75) Inventors: Nobuaki Taniguchi, Ibaraki (JP); Isao Kinoyama, Ibaraki (JP); Takashi Kamikubo, Ibaraki (JP); Akira Toyoshima, Ibaraki (JP); Kiyohiro Samizu, Ibaraki (JP); Eiji Kawaminami, Ibaraki (JP); Masakazu Imamura, Ibaraki (JP); Hiroyuki Moritomo, Ibaraki (JP); Akira Matsuhisa, Ibaraki (JP); Masaaki Hirano, Ibaraki (JP); Yoji Miyazaki, Ibaraki (JP); Eisuke Nozawa, Ibaraki (JP); Minoru Okada, Ibaraki (JP); Hiroshi Koutoku, Ibaraki (JP); Mitsuaki Ohta, Ibaraki (JP)

(73) Assignee: Yamanouchi Pharmaceutical Co. Ltd., Tokyo (JP)

( * ) Notice: Subject to any disclaimer, the term of this patent is extended or adjusted under 35 U.S.C. 154(b) by 0 days.

(21) Appl. No.: 09/787,672

(22) PCT Filed: Sep. 21, 1999

(86) PCT No.: PCT/JP99/05149

§ 371 (c)(1),
(2), (4) Date: Mar. 21, 2001

(87) PCT Pub. No.: WO00/17163

PCT Pub. Date: Mar. 30, 2000

(30) Foreign Application Priority Data

Sep. 22, 1998 (JP) .......................... 10-267508
Jun. 2, 1999 (JP) .......................... 11-155398

(51) Int. Cl.$^7$ ..................... C07D 231/74; C07D 273/88; C07D 215/38; A61K 31/415; A61K 31/495
(52) U.S. Cl. .................. 514/253.01; 544/395; 544/360; 544/390; 514/255.03; 514/255.01
(58) Field of Search ................. 544/395, 360, 544/390; 514/255.03, 253.01, 255.01

(56) References Cited

U.S. PATENT DOCUMENTS

| | | | |
|---|---|---|---|
| 4,797,401 A | 1/1989 | Kemp et al. | ................. 514/255 |
| 5,411,981 A | 5/1995 | Gaillard-Kelly et al. | .... 514/386 |
| 5,442,064 A | 8/1995 | Pieper et al. | ................ 544/360 |

FOREIGN PATENT DOCUMENTS

| | | | | |
|---|---|---|---|---|
| AU | 60362/80 | 1/1981 | ......... | C07D/295/14 |
| DE | 1239940 | * 5/1967 | | |
| EP | 0 023 569 | 2/1981 | ......... | C07D/295/14 |

(List continued on next page.)

OTHER PUBLICATIONS

E. Ravina et al., Synthesis and Potential Anthelminitic Activity of Methyl–5–(4–salicyloyl–piperazin–1–yl)–benzimidazole–2–carbamates, Arzneim.–Forsch. (1993), 43(6), pp. 689–694.

Khim. Far. Zh. (1988), 22(6), pp. 696–699.

Rashmi Dubey et al., Synthesis and Anthelminitic Activity of 5(6)–(Benzimidazol–2–ylcarbamoyl) and (4–Substituted piperazin–1–yl) benzimidazoles[1], J. Med. Chem. (1985), 28(11), pp. 1748–1750.

S. Abuzar et al., Synthesis of 2–carbalkoxyamino–5(6)–(1–substituted piperazine–4–yl/piper–azin–4–ylcarbonyl)benzimidazoles and Related Compounds as Potential Anthelmintics[1], (1984), pp. 747–749.

Von H. Loewe et al., Basisch substituierte 2,6–Bis–benzimidazolderivate, eine neue chemotherapeutisch aktive Korperklasse[1], Arzneim.–Forsch. (1974), 24(12), pp. 1927–1933.

B. A. Kysheyoe, et al., Zh. Org. Khim. (1987), 23(3), pp. 637–642.

CAS printout for Griss et al.*
CAS printout for Honda et al.*
International Search Report.

Ravi, R et al, "Nucleophilic substitutions on 3–chloro–4–fluoronitrobenzene", Indian Journal of Chemistry, vol. 36B, No. 4, Apr. 1997, pp. 347–348.

Ogawa, Hidenori et al, "Studies on Positive Inotropic Agents. VI[1]) Synthesis of 1–Aromatic Ring Substituted 4–(3,4–Dimethoxybenzoyl)–piperazine Derivatives", Chem Pharm Bull., vol. 36, No. 7, pp. 2401–2409.

Miyamoto, Teruyuki et al., "Pyridonecarboxylic Acids as Antibacterial Agents. VIIII.[1]) An Alternative Synthesis of Enoxacin via Fluronicotinic Acid Derivatives", Chem Pharm Bull., vol. 35, No. 6, pp. 2280–2285.

Agrawal, VK et al, "Studies in Potential Filaricides: Part XV†–Synthesis of 1–Acyl/Aryl–4–substituted–piperazines as Diethylcarbamazine Analogs‡", Indian Journal of Chemistry, vol. 23B, No. 7, Jul. 1984, pp. 650–654.

Zhang, X.; Li, G.; Dai, Z. ; Qian, Y.' Chen, L. Synthesis and Antimararial Effects of Some Derivatives of 2,4–Diamino–6–Substituted Piperazinylquinazolines. Xaozue Xuebao, vol. 16, No. 6, pp. 415–424 (1981) (copy submitted to USPTO by WIPO).

Registry No. 82596–31–4 1–(3–cyano–4–nitrophenyl)–4–(methylsulphenyl)–piperazine (copy submitted to USPTO by WIPO).

Registry No. 82596–32–5 1–(3–cyano–4–nitrophenyl)–4–[(4–methylfonyl)–sulfonyl)] piperazine (copy submitted to USPTO by WIPO).

Chemical Abstracts vol. 97, Abstract No. 97:109953 (1981).

Primary Examiner—Richard L. Raymond
Assistant Examiner—Hong Liu
(74) Attorney, Agent, or Firm—Sughrue Mion, PLLC

(57) ABSTRACT

This application relates to a piperazino-substituted novel cyanophenyl derivative in which a substituted carbamoyl or substituted sulfamoyl group having an aryl, heterocyclic or the like group that may have a substituent group is bonded to one nitrogen atom on the piperazine ring. The compound of this application has an anti-androgen action and is useful in preventing or treating prostatic cancer, benign prostatic hyperplasia and the like diseases.

7 Claims, No Drawings

FOREIGN PATENT DOCUMENTS

| | | | |
|---|---|---|---|
| JP | 63-44572 | 2/1988 | ......... C07D/295/12 |
| WO | 95/17471 | 6/1995 | ........... C09B/31/08 |
| WO | WO 95/25443 | 9/1995 | |
| WO | WO 96/02525 | 2/1996 | |
| WO | WO 96/21648 | 7/1996 | |
| WO | WO 97/02245 | 1/1997 | |
| WO | 97/03054 | 1/1997 | ......... C07D/221/08 |
| WO | WO 97/19089 | 5/1997 | |
| WO | WO 98/00402 | 1/1998 | |
| WO | WO 98/42696 | 10/1998 | |

* cited by examiner

CYANOPHENYL DERIVATIVE

TECHNICAL FIELD

This invention relates to novel cyanophenyl derivatives useful as medicaments, particularly as an anti-androgen, and salts and pharmaceutical compositions thereof.

BACKGROUND ART

Androgen as a steroid hormone is secreted from testis and adrenal cortex and induces male sex hormone actions. Androgen, when incorporated into target cells, acts upon an androgen receptor and the receptor to which androgen binds forms a dimer. Subsequently, this dimer binds to an androgen-response-element on DNA to accelerate synthesis of mRNA and to thereby induce proteins which control the androgen actions, thus expressing various actions within living organism (*Prostate Suppl.*, 6, 1996, 45–51, Trends in Endocrinology and Metabolism, 1998, 9 (8), 317–324).

Prostatic cancer, benign prostatic hyperplasia, virilism, hirsutism, baldness, acne, seborrhea and the like can be exemplified as diseases which are progressed by androgen. Accordingly, anti-androgens are used for the treatment of these diseases in which androgen is concerned.

Anti-androgens, which have substrate resembling steroidal structure or nono-steroidal structure are currently used in the clinical field. Though chlormadinone acetate and the like are known as the steroidal anti-androgen, it is known that, since separation of actions of these compounds from other steroids having similar structures is not sufficient, they cause changes in the blood hormone level and induces serious side effects such as reduction of libido and the like (*Jpn. J. Clin. Oncol.*, 1993, 23 (3), 178–185). On the other hand, flutamide (JP-A-49-81332; the term "JP-A" as used herein means an "unexamined published Japanese patent application"), bicalutamide (GB 8221421, WO 95/19770) and the like acylanilide derivatives are known as non-steroidal anti-androgens, but their anti-androgenic actions are not sufficient. Thus, combined therapy with an LH-RH agonist is usual for the treatment of prostatic cancer (Nipponrinsho, 1998, 56 (8), 2124–2128).

Regarding the compounds having piperazinocyanophenyl skeletons, substances having oxitocin and vasopressin receptor antagonism are disclosed in WO 95/25443, and substances having 5HT receptor antagonism in WO 96/02525, substances as intercellular mutual action inhibitors in DE 4234295, substances as production intermediates of cell adhesion inhibitors in WO 97/2245 and substances having antitumor actions in WO 98/00402 and WO 98/21648, but they do not disclose or suggest on anti-androgen actions.

DISCLOSURE OF THE INVENTION

The object of the invention is to provide a novel cyanophenyl derivative and salts thereof having strong anti-androgen actions and to further provide medicaments containing the same.

With the aim of solving the aforementioned problems incidental to the existing anti-androgens, the inventors of the invention have conducted intensive studies and found unexpectedly that a novel cyanophenyl derivative to which a substituted carbamoyl or substituted sulfamoyl group is bound has strong anti-androgen actions and good oral activities, thus resulting in the accomplishment of the invention.

Accordingly, the invention relates to a cyanophenyl derivative represented by the following general formula (I) or a salt thereof

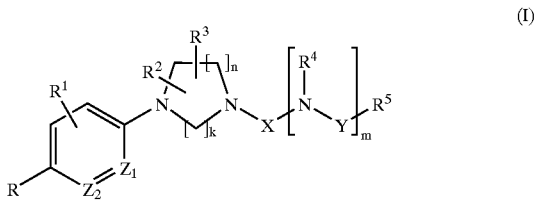

wherein each symbol has the following meaning,
R: cyano or nitro group,
$R^1$: a hydrogen atom, a halogen atom or a cyano, halogeno-lower alkyl, vitro, carboxyl, lower alkyl, $R^6$—A—, $R^7$—S(O)$_p$—, lower alkyl-C(=O)— or lower alkyl-O—C(=O)— group,
$R^2$, $R^3$ and $R^4$: these may be the same or different from one another and each means a hydrogen atom, a lower alkyl group, a carbamoyl group which may be substituted by 1 or 2 lower alkyl groups, a lower alkyl-C(=O)—, lower alkyl-O—C(=O)— group, wherein $R^2$ and $R^3$ bind to optional carbon atoms on the ring,
$R^5$: a lower alkyl; aryl-lower alkyl-O—; carboxyl; lower alkyl-O—C(=O)—; amido which may be substituted by 1 or 2 lower alkyl groups; or aryl, heterocyclic or cycloalkyl group which may have a substituent group; N($R^{13}$)$R^{14}$-lower alkyl-O—; with the proviso that when m=1, $R^4$ and $R^5$ may together form a five- or six-membered heterocycle which may have other hetero atom,
$R^6$: a halogeno-lower alkyl; aryl; or lower alkyl which may be substituted by N(R)$R^{10}$, OH or lower alkyl-O—,
$R^7$: a lower alkyl, aryl or N($R^{11}$)$R^{12}$—,
$R^8$, $R^9$, $R^{10}$, $R^{11}$, $R^{12}$, $R^{13}$ and $R^{14}$: hydrogen, lower alkyl or aryl, with the proviso that $R^6$ and $R^8$, $R^9$ and $R^{10}$ or $R^{13}$ and $R^{14}$ may together form a nitrogen-containing cycloalkyl which may have other hetero atom and may have la substituent group,
k or n: 1, 2 or 3,
m: 0 or 1,
p: 0, 1 or 2,
A: an oxygen atom or NR$^8$,
X=—C(=O)—, —C(=S)— or —S(O)$_2$— group,
Y: a bond, lower alkylene, —C(=O)— or —S(O)$_2$— group, with the proviso that, when $R^5$ is a lower alkyl group, Y is a group other than lower alkylene, and $Z_1$ or $Z_2$: these may be the same or different from each other and each means CH or nitrogen atom,
with the proviso that 1) when $R^1$ is hydrogen atom, at least one of $R^2$ and $R^3$ is a lower alkyl, 2) when R is a nitro group, X is —C(=O)— or —S(O)$_2$—, and n is 1, k is 2 and m is 0, at least one of $R^2$ and $R^3$ is a group other than a hydrogen atom, and 3) when R is a cyano group, $Z_1$ is a nitrogen atom, and X is —C(=O)— and n is 1, k is 2, m is 0, and $R^5$ is a methyl group, $R^1$ is a group other than a fluorine atom.

Preferred is a cyanophenyl derivative or a salt thereof according to the first aspect of the invention, wherein R is a cyano group;
also preferred is a cyanophenyl derivative or a salt thereof according to the first aspect of the invention, wherein $R^1$ is a halogen atom, cyano, halogeno-lower alkyl, nitro or lower alkyl-O—; $R^2$ and $R^3$: at least one of them is a lower alkyl group; $R^4$: a hydrogen atom or a lower alkyl group; $R^5$: an aryl, heterocyclic or cycloalkyl group which may have substituent(s) group; k is 2, n is 1; m is 1, X is —C(=O)— group; Y is a bond; and $Z_1$ or $Z_2$ both means CH;

more preferred is a cyanophenyl derivative according to the first or second aspect of the invention, wherein the substituent group of the aryl, heterocyclic or cycloalkyl group of $R^5$ which may have substituent(s) is a radical selected from the group consisting of a halogen atom, halogeno-lower alkyl, lower alkyl, lower alkyl-O—, lower alkyl-S—, lower alkyl-S(=O)—, lower alkyl-S(O)$_2$—, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O-C(=O)—, aryl-O—, amino-O—, carbamoyl which may be substituted by a lower alkyl, carboxyl, lower alkyl-O— C(=O)—, heterocyclic and OH group; and most preferred is a compound, or a salt thereof, selected from (2R,5S)4-(4-cyano-3-trifluoromethylphenyl)-N-(6-methoxy-3-pyridyl)-2,5-dimethylpiperazine-1-carboxamide; (2R,5S)-N-(2-amino-pyrimidin-4-yl)-4-(4-cyano-3-trifluoromethylphenyl)-2,5-dimethylpiperazine-1-carboxamide; (2R,5S)-4-(4-cyano-3-trifluoromethylphenyl)-2,5-dimethyl-N-(6-trifluoromethyl-3-pyridyl)piperazine-1-carboxamide; (2R,5S)-4-(4-cyano-3-trifluoromethylphenyl)-N-(2-fluoro-4-pyridyl)-2,5-dimethylpiperazine-1-carboxamide; and (2R,5S)-N-(2-bromo-4-pyridyl)-4-(4-cyano-3-trifluoromethylphenyl)-2,5-dimethylpiperazine-1-carboxamide.

Another object of the invention is a pharmaceutical composition which comprises the cyanophenyl derivative of general formula (I) or a salt thereof as the active ingredient;

preferably an anti-androgen agent which comprises the cyanophenyl derivative of general formula (I) or a salt thereof as the active ingredient; and more preferably a therapeutic agent for diseases which are progressed by androgen, which comprises the cyanophenyl derivative of general formula (I) or a pharmaceutically acceptable salt thereof as the active ingredient, wherein the diseases which are progressed by androgen include prostatic cancer, benign prostatic hyperplasia, virilism, hirsutism, baldness, acne and seborrhea.

Most preferred is a pharmaceutical composition for the treatment of prostatic cancer and benign prostatic hyperplasia, which comprises the cyanophenyl derivative of general formula (I) or a pharmaceutically acceptable salt thereof as the active ingredient.

The following further describes the compound represented by general formula (I).

In the definition of general formula of the invention, the term "lower" means a straight or branched carbon chain having from 1 to 6 carbon atoms unless otherwise noted.

The group $R^2$ or $R^3$ binds to the same or different optional carbon atom on the saturated ring containing two nitrogen atoms.

The aryl, heterocyclic or cycloalkyl group which may have a substituent group may have from 1 to 3 substituent groups on the ring, preferably a halogen atom, halogeno-lower alkyl, lower alkyl, lower alkyl-O—, lower alkyl-S—, lower alkyl-S (=O)—, lower alkyl-S(O)$_2$—, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O—C(=O)—, aryl-O—, amino-O—, carbamoyl which may be substituted by 1 or 2 lower alkyl or carboxyl or lower alkyl-O—C(=O)—, heterocycle which may have a substituent group or OH group.

The "lower alkyl" is desirably a straight or branched-chain lower alkyl group having from 1 to 6 carbon atoms, and its examples include methyl, ethyl, n-propyl, isopropyl, n-butyl, isobutyl, sec-butyl, tert-butyl, n-pentyl, n-hexyl and the like.

As substituent group of the lower alkyl-O— which may have a substituent group, aryl group or the like substituent group can be exemplified.

The "lower alkylene" is desirably a straight or branched-chain lower alkylene group having from 1 to 6 carbon atoms, and its examples include methylene, ethylene, propylene, isopropylene, butylene, pentamethylene, hexamethylene and the like, of which an alkylene having from 1 to 3 carbon atoms is preferred.

The "aryl" is desirably an aromatic hydrocarbon radical having from 6 to 12 carbon atoms, and its examples include phenyl, α-naphthyl, β-naphthyl, biphenylyl and the like. More preferred are those which have from 6 to 10 carbon atoms.

As the "halogen atom", fluorine, chlorine, bromine or iodine atom can be defined.

The aforementioned $C_{1-6}$ alkyl group is desirable as the lower alkyl group of the "halogeno-lower alkyl", and examples of the halogeno-$C_{1-6}$ alkyl group include fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl, 2-iodoethyl and the like, of which trifluoromethyl is preferred.

The "cycloalkyl group" is desirably a three- to eight-membered alicyclic hydrocarbon radical having from 3 to 10 carbon atoms, and its examples include cyclopropyl, cyclobutyl, cyclopentyl, cyclohexyl, cycloheptyl, cyclooctyl and the like.

The "heterocycle" means a five- or six-membered heteroaryl group or saturated heterocycle containing from 1 to 4 hetero atoms selected from nitrogen atom, oxygen atom and sulfur atom, or a bicyclic heteroaryl group condensed with benzene ring or other heterocycle, and examples of the heteroaryl group include pyrrole, imidazole, pyrazole, pyridine, pyrazine, pyrimidine, pyridazine, triazole, thiophene, thiopyran, furan, pyran, dioxolane, thiazole, isothiazole, thiadiazole, thiazine, oxazole, isoxazole, oxadiazole, furazane, dioxazole, oxazine, oxadiazine, dioxazine and the like, examples of the saturated heterocycle include pyrrolidinyl group, piperidinyl group, piperazinyl group, morpholyl group, thiomorpholyl group and the like, and examples of the condensed heteroaryl include indole, isoindole, indazole, quinoline, quinazoline, quinoxaline, isoquinoline, benzimidazole, benzothiophene, benzothiazole, benzofuran, benzofurazane, imidazopyridine, imidazopyrazine, pyridopyridine, phthalazine, naphthyridine, indolizine, purine, quinolizine, cinnoline, isochroman, chroman and the like. Preferred is pyridine, pyrimidine, thiophene, furan or the like five- or six-membered heteroaryl group having 1 or 2 hetero atoms selected from nitrogen atom, oxygen atom and sulfur atom.

The term "when m=1, $R^4$ and $R^5$ may together form a five- or six-membered heterocycle which may have other hetero atom" means a five- or six-membered heteroaryl group or saturated heterocycle having from 1 to 3 hetero atoms selected from nitrogen atom, oxygen atom and sulfur atom, and it may have oxo group or the like substituent group. Illustratively, examples of the heteroaryl include pyrrole, imidazole, pyrazole, pyridine, pyrazine, pyrimidine, pyridazine, triazole and the like, and examples of the saturated heterocycle include pyrrolidinyl group, piperidinyl group, piperazinyl group, morpholyl group, thiomorpholyl, 1,4-diazepan, thiomorpholine-1-oxido, thiomorpholine-1,1-dioxido, 1,4-oxazepan group and the like. Preferred is a five- or six-membered saturated heterocycle having 1 hetero atom selected from nitrogen atom, oxygen atom and sulfur atom, in addition to the nitrogen atom to which $R^4$ is bonded, and more preferred in thiomorpholino group.

The term "$R^6$ and $R^8$, $R^9$ and $R^{10}$ or $R^{13}$ and $R^{14}$ can together form a nitrogen-containing cycloalkyl which may have other hetero atom and may have substituent group(s)" means a five- or six-membered saturated heterocycle having 1 hetero atom selected from nitrogen atom, oxygen atom and sulfur atom, in addition to the nitrogen atoms to which $R^6$ and $R^8$, $R^9$ and $R^{10}$ or $R^{13}$ and $R^{14}$ are bonded, and it may also have 1 or 2 substituent groups such as oxo group, lower alkyl, aryl and the like. Preferred is pyrrolidino, piperidino, morpholino, piperazine or thiomorpholino group.

Among the compounds of the invention, in the case of a compound which has a tertiary amine or sulfide, the nitrogen atom or sulfur atom may be converted into oxido at an appropriate oxidation state, and all of these oxido derivatives are included herein.

Geometrical isomers based on the amido bond exist in the compound (I) of the invention. Depending on the kind of substituent group, it may have an asymmetric center or axial asymmetry of one or more carbon, nitrogen, sulfur and the like in some cases, and (R) isomer, (S) isomer and the like optical isomers, racemic modification, diastereomers and the like exist based thereon. Also, depending on the kind of substituent group, it may have double bond, so that geometrical isomers such as (Z) isomer, (E) isomer and the like, as well as cis-form and trans-form based on cyclohexane and the like, are present. All of the separated or mixed form of these isomers are included in the invention.

The compound of the invention forms a salt. Illustratively, it is an acid addition salt with an inorganic acid or an organic acid or a salt with an inorganic or organic base, and a pharmaceutically acceptable salt is desirable. Illustrative examples of the salt include addition salts with hydrochloric acid, hydrobromic acid, hydroiodic acid, sulfuric acid, nitric acid, phosphoric acid and the like mineral acids, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, toluenesulfonic acid and the like organic acids or aspartic acid, glutamic acid and the like acidic amino acids, and salts with sodium, potassium, magnesium, calcium, aluminum, lithium and the like inorganic bases, methylamine, ethylamine, ethanolamine and the like organic bases or lysine, ornithine and the like basic amino acids. It may also be in the form of a quaternary ammonium salt. Illustrative examples of the quaternary ammonium salt include a lower alkyl halide, a lower alkyl triflate, a lower alkyl tosylate, a benzyl halide and the like, of which methyl iodide, benzyl chloride or the like is preferred.

In addition, the compound of the invention can form a hydrate, a solvate with ethanol or the like and polymorphism.

(Production Methods)
First production method

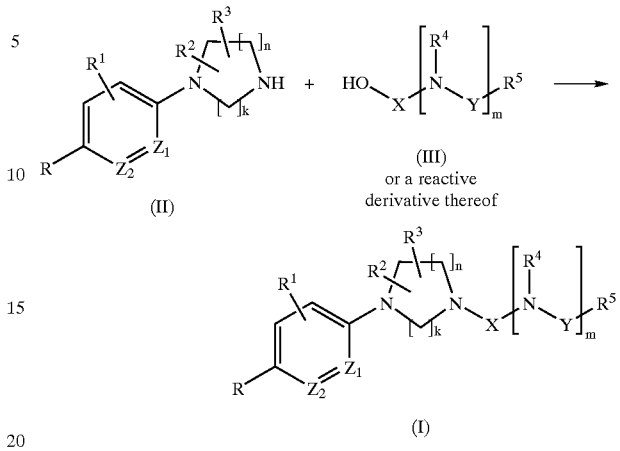

(Symbols in the formula are as defined in the foregoing.)

This production method is a method in which the compound (I) of the invention is produced by allowing a substituted amine represented by the general formula (II) or a salt thereof to react with a compound represented by the general formula (III) or a reactive derivative thereof and then, if there is a protecting group, removing the protecting group.

Examples of the reactive derivative of the compound (III) include usual carboxylic acid esters such as methyl ester, ethyl ester, isobutyl ester, tert-butyl ester and the like; its phenylesters such as p-nitrophenyl ester and the like; its acid halides such as chloride, acid bromide and the like, acid azide, its active esters obtained by allowing it to react with a phenolic compound such as 2,4-dinitrophenol and the like phenol compounds or 1-hydroxysuccinimide, 1-hydroxybenzotriazole (HOBt) and the like N-hydroxyamine compounds; its symmetric anhydrides; its mixed acid anhydrides including organic acid based mixed acid anhydrides obtained by reacting with acid anhydrides, alkyl carboxylate halide and the like halocarboxylic acid alkyl esters or pivaloyl halides, and phosphoric acid based mixed acid anhydrides obtained by the combination of triphenylphosphine and the like organic phosphorus compounds with N-bromosuccinimide and the like activating agents, as well as sulfonyl chloride and isocyanate.

In addition, when a carboxylic acid is allowed to react as free acid or an active ester is allowed to react without isolation, it is desirable to use dicyclohexylcarbodiimide (DCC), carbonyldiimidazole, diphenylphosphoryl azide, diethylphosphoryl cyanide, 1-ethyl-3-(3-dimethylaminopropyl)carbodiimide hydrochloride (WSC) or the like condensing agent.

According to the invention, an acid chloride method, a method in which the reaction is carried out in the coexistence of an active esterification agent and a condensation reaction with an isocyanate or a thioisocyanate are particularly advantageous.

In this connection, the isocyanate can be synthesized from a carboxylic acid, an amide, an acid hydrazide or the like carboxylic acid derivative making use of a known rearrangement reaction. When converted into isocyanate from a carboxylic acid, it is advantageous to use a method in which the carboxylic acid is once converted into an acid chloride, a mixed acid anhydride or the like and then allowed to react with sodium azide or the like to obtain an acid azide which is subsequently converted into an isocyanate by heating or the like means. Also, when diphenylphosphoryl azide (DPPA) is used in this method, it is possible to convert the carboxylic acid into an isocyanate by one reaction. It is also possible to obtain the compound (I) by allowing DPPA to undergo the reaction in the coexistence of the carboxylic acid and compound (II). On the other hand, it is possible to obtain isocyanate by allowing a corresponding amine derivative to react with phosgene or a phosgene-equivalent compound. Examples of the phosgene-equivalent compound include phosgene dimer, triphosgene, carbonyldiimidazole and a combination of di-tert-butyl carbonate (DIBOC) with 4-(N,N-dimethylamino)pyridine (DMAP). Also, the thioisocyanate can be synthesized making use of a known reaction using thiophosgene, thiocarbonyldiimidazole or the like.

In addition, it is possible to obtain the compound (I) by once converting a corresponding amine derivative into an active intermediate having a leaving group typified by phenyl carbonate and then allowing it to react with the compound (II).

Though it varies depending on the used reactive derivative, condensing agent and the like, the reaction is generally carried out in an inert organic solvent including dichloromethane, dichloroethane, chloroform and the like halogenated hydrocarbons, benzene, toluene, xylene and the like aromatic hydrocarbons, ether, tetrahydrofuran and the like ethers, ethyl acetate and the like esters, acetonitrile, N,N-dimethylformamide (DMF), N,N-dimethylacetamide, N-methylpyrrolidone, dimethylimidazolidinone and the like, under cooling, under cooling to room temperature or under room temperature to heating, depending on the reactive derivative.

In carrying out the reaction, in order to progress the reaction smoothly, it is advantageous in some cases to use the substituted amine (II) in excess amount or to carry out the reaction in the presence of N-methylmorpholine, trimethylamine, triethylamine, N,N-dimethylaniline, pyridine, DMAP, picoline, lutidine, collidine, 1,8-diazabicyclo[5.4.0]undec-7-ene (DBU) or the like base. Pyridine or the like can also be used as the solvent.

In this case, it is desirable in some cases that the oxygen, sulfur, nitrogen or the like atom existing in the molecule is bonded with a protecting group, and the protecting groups described in "Protective Groups in Organic Synthesis", second edition, edited by Greene and Wuts, can be exemplified as the protecting group and used by optionally selecting them depending on the reaction conditions.

Second production method

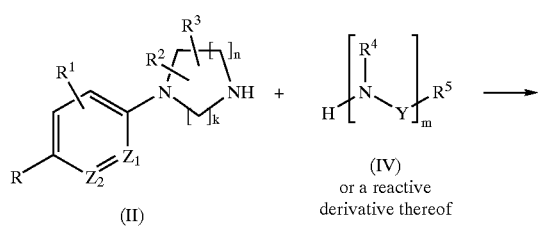

(II)

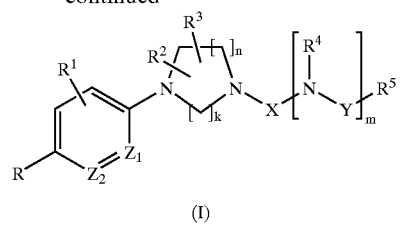

(I)

(Symbols in the formula are as defined in the foregoing.)

This production method is a method in which the compound (I) of the invention is produced by allowing a substituted amine represented by the general formula (II) or a salt thereof to react with an X-containing or equivalent reactive compound and then to react with a compound represented by the general formula (IV), subsequently removing a protecting group if there is a protecting group.

When the product is a urea derivative, phosgene, phosgene dimer, triphosgene, carbonyldiimidazole or a known equivalent compound can be used as the X-containing or equivalent reactive compound. When the product is a sulfamide derivative, sulfamide, sulfuryl chloride or the like known reagent can be used.

In carrying out the reaction, the conditions shown in the first production method can be employed.

Third production method

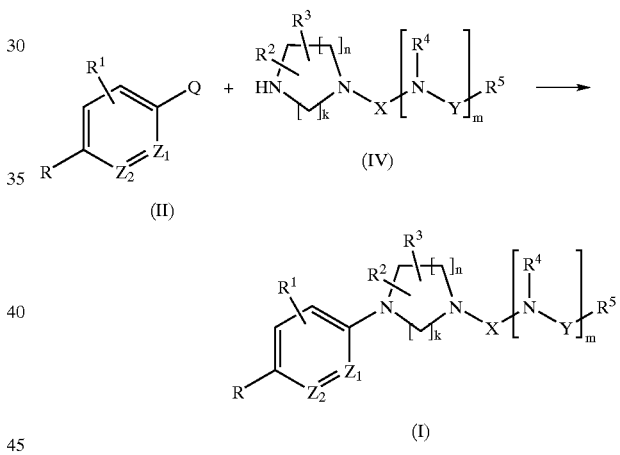

(In the formula, Q means fluorine, chlorine, bromine, iodine or the like halogen or trifluoromethane sulfonate, benzene sulfonate or the like leaving group.)

This production method is a method in which the compound (I) of the invention is produced by allowing a substituted amine represented by the general formula (VI) or a salt thereof to react with a compound represented by the general formula (V).

In carrying out the reaction, in order to progress the reaction smoothly, it is advantageous in some cases to use the substituted amine (VI) in excess amount or to carry out the reaction in the presence of N-methylmorpholine, trimethylamine, triethylamine, diisopropylethylamine, N,N-dimethylaniline, pyridine, DMAP, picoline, lutidine, collidine, 1,8-bistrimethylaminonaphthalene, DBU or the like organic base or potassium carbonate, sodium carbonate, calcium carbonate, sodium bicarbonate, sodium hydroxide, cesium carbonate or the like inorganic base. Pyridine or the like can also be used as the solvent. In some cases, it may be effective to use some organometallic catalysts to accelerate a reaction. Though it varies depending on the used substrate and conditions, the reaction is generally carried out in an inert organic solvent including dichloromethane, dichloroethane, chloroform and the like halogenated hydrocarbons, benzene, toluene, xylene and the like aromatic hydrocarbons, ether, tetrahydrofuran and the like ethers, ethyl acetate and the like esters, ethanol, methanol and the like alcohol solvents, acetonitrile, DMF, N,N-dimethylacetamide, N-methylpyrrolidone, N,N-dimethylimidazolidinone, dimethyl sulfoxide and the like, under cooling, under cooling to room temperature or under room temperature to heating, depending on the reactive derivative.

Fourth production method

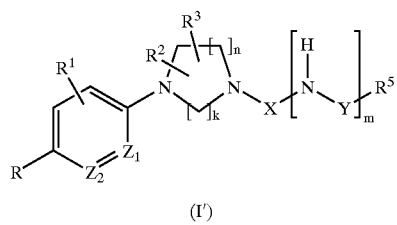

(I')

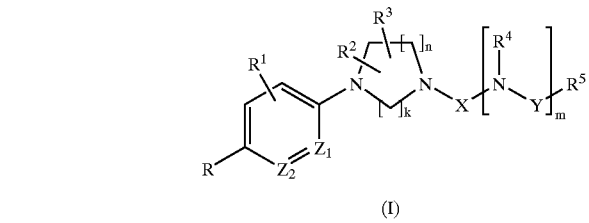

(I)

(Symbols in the formula are as defined in the foregoing.)

This production method is a method in which the compound (I) of the invention is produced by the alkylation or acylation of a compound of the invention represented by the general formula (I': $R^4$=H).

In this reaction, it is possible to use an alkylation agent such as methyl iodide, ethyl iodide, benzyl bromide or the like alkyl halide, dimethyl sulfate or the like sulfuric ester and methane sulfonate, methyl trifluoromethanesulfonate or the like sulfonate. Alternatively, an acylation agent such as acetyl chloride or the like acid chloride or acetic anhydride or the like acid anhydride is used. In this case, triethylamine, diisopropylethylamine, pyridine, lithium diisopropylamide, sodium hexamethyldisilazide or the like organic base or sodium carbonate, potassium carbonate, calcium carbonate, sodium bicarbonate, sodium hydroxide, sodium hydride or the like inorganic base may be used.

The reaction is generally carried out in an inert organic solvent including dichloromethane, dichloroethane, chloroform and the like halogenated hydrocarbons, benzene, toluene, xylene and the like aromatic hydrocarbons, ether, tetrahydrofuran and the like ethers, ethyl acetate and the like esters, DMF, N,N-dimethylacetamide, dimethyl sulfoxide and the like, under cooling, under cooling to room temperature or under room temperature to heating, depending on the reactive derivative.

Fifth production method

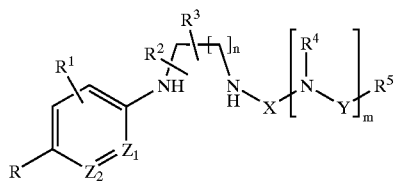

(VII)

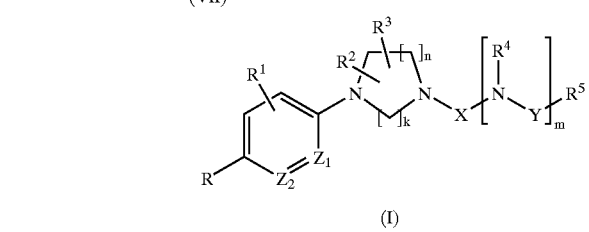

(I)

(Symbols in the formula are as defined in the foregoing.)

This production method is a method in which the compound (I) of the invention is produced by cyclization of a compound represented by the general formula (VII).

In this reaction, aldehyde or ketone and acetal, ketal, thioketal or the like carbonyl equivalent compound are used in the cyclization. In general, an acidic condition or a basic condition can be used in the reaction which is generally carried out in an inert organic solvent including dichloromethane, dichloroethane, chloroform and the like halogenated hydrocarbons, benzene, toluene, xylene and the like aromatic hydrocarbons, ether, tetrahydrofuran and the like ethers, ethyl acetate and the like esters, DMF, N,N-dimethylacetamide, dimethyl sulfoxide and the like, under cooling, under cooling to room temperature or under room temperature to heating, depending on the reactive derivative. Acetic acid, trifluoroacetic acid or the like organic acid is particularly suitable.

The compound of the invention synthesized in accordance with the above methods can be converted into other compounds of the invention by the conversion of functional groups and the like by using known reactions, and some of them were described in Examples.

The thus produced compound of the invention is isolated and purified as its free form, a salt thereof, a hydrate thereof, a solvate thereof or as a polymorphic substance. A salt of the compound (I) of the invention can also be produced by subjecting it to a usual salt formation reaction.

The isolation and purification are carried out by employing extraction, concentration, evaporation, crystallization, filtration, recrystallization, various types of chromatography and the like usual chemical operations.

Various types of isomers can be selectively synthesized by using appropriate starting materials, reagents or reaction conditions, or separated by making use of the difference in physical properties among isomers. For example, each optical isomer can be prepared as a stereochemically pure isomer by selecting appropriate materials or separated by an optical resolution of racemic compounds (e.g., a general method in which they are converted into diastereomer salts with an optically active base and then subjected to optical resolution).

A pharmaceutical preparation which contains one or more of the compounds of the invention or salts thereof as the active ingredient is prepared using carriers, fillers and other additives generally used in the preparation of medicaments.

It may be administered either by oral administration through tablets, pills, capsules, granules, powders, solutions or the like, or by parenteral administration through intravenous injection, intramuscular injection and the like injections, suppositories, percutaneous preparations and the like. Its dose is optionally decided by taking symptoms, age and sex of the patient to be treated and the like into consideration, but generally, it is approximately from 0.01 to 50 mg per day per adult in the case of oral administration or approximately from 0.001 to 5 mg per day per adult in the case of parenteral administration, and the daily dose is administered once a day or by dividing it into 2 to 4 doses per day.

The solid composition for use in the oral administration according to the invention is used in the tablets, powders, granules and the like forms. In such a solid composition, one or more active substances are mixed with at least one inert diluent such as lactose, mannitol, glucose, hydroxypropylcellulose, microcrystalline cellulose, starch, polyvinyl pyrrolidone, metasilicate or magnesium aluminate. In the usual way, the composition may contain additives other than the inert diluent, which include a lubricant such as magnesium stearate, a disintegrating agent such as calcium cellulose glycolate, a stabilizing agent such as lactose and a solubilization assisting agent such as glutamic acid or aspartic acid. As occasion demands, tablets or pills may be coated with a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, this composition may also contain auxiliary agents such as a moistening agent and a suspending agent, as well as a sweetener, a flavor, an aromatic and an antiseptic.

The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, olive oil or the like plant oil, ethanol or the like alcohol, polysorbate 80 (trade name) and the like. Such a composition may further contain auxiliary agents such as an antiseptic, a moistening agent, an emulsifying agent, a dispersing agent, a stabilizing agent (e.g., lactose) and a solubilization assisting agent (e.g., glutamic acid or aspartic acid). These compositions are sterilized for example by filtration through a bacteria retaining filter, blending of a germicide or irradiation. Alternatively, they may be used by firstly making into sterile solid compositions and dissolving them in sterile water or a sterile solvent for injection use prior to their use.

[EXAMPLES]

The following describes the invention more illustratively with reference to examples. The invention is not limited to these examples. In this connection, production methods of the starting materials compounds to be used in the examples are described as reference examples.

Reference Example 1-1 trans-4-(2,5-Dimethylpiperazin-1-yl)-2-trifluoromethylbenzonitrile

A 1 g portion of 4-fluoro-2-trifluoromethylbenzonitrile and 2.4 g of trans-2,5-dimethylpiperazine were dissolved in 30 ml of DMF and heated at 80° C. for a whole day and night. The reaction solution was mixed with water, extracted with ethyl acetate and dried over anhydrous sodium sulfate, and then the solvent was evaporated under reduced pressure. The residue was purified by a silica gel column chromatography, and 1.3 g of the title compound was obtained from chloroform-methanol (10:1, v/v) eluate.

Compounds of Reference Examples 1-2 to 1-17 were synthesized in the same manner as described in Reference Example 1-1. Their structures and physical data are shown in Tables 1 to 3.

Reference Example 2

Synthesis of t-butyl 3-methylpiperazine-1-carboxylate

Under ice-cooling, 15 ml of tetrahydrofuran (THF) solution containing 10.9 g of DIBOC was added to 150 ml of THF solution containing 10 g of 2-methylpiperazine. After stirring overnight, the solvent was evaporated under reduced pressure. The residue was mixed with water and extracted with ethyl acetate, and then the organic layer was washed and dried and the solvent was evaporated under reduced pressure to obtain 8.94 g of the title compound as a yellow oily substance.

Reference Example 3 t-Butyl 4-(4-cyano-3-trifluoromethylphenyl)-3-methylpiperazine-1-carboxylate

A 4.46 g portion of t-butyl 3-methylpiperazine-1-carboxylate synthesized in Reference Example 2, 6.74 g of 4-fluoro-2-trifluoromethylbenzonitrile and 7.76 ml of diisopropylethylamine were stirred in 50 ml of DMF at 100° C. for 2 days. The reaction solution was diluted with water and extracted with ethyl acetate, the organic layer was washed and dried and then the solvent was evaporated under reduced pressure. The residue was subjected to a silica gel column chromatography and eluted with hexane-ethyl acetate (3:1, v/v) to obtain 5.6 g of the title compound as white crystals.

Reference Example 4

4-(2-Methylpiperazin-1-yl)-2-trifluoromethylbenzonitrile

A 2.85 g portion of t-butyl 4-(4-cyano-3-trifluoromethylphenyl)-3-methylpiperazine-1-carboxylate synthesized in Reference Example 3 was stirred in 50 ml of trifluoroacetic acid at 0° C. to room temperature for 2 hours. The solvent was evaporated under reduced pressure, the resulting residue was neutralized with saturated aqueous sodium bicarbonate and then extracted with ethyl acetate, the organic layer was washed and dried and then the solvent was evaporated under reduced pressure. The residue was purified by a silica gel column chromatography, and 5.6 g of the title compound was obtained from chloroform-methanol-28% aqueous ammonia (10:1:0.1, v/v/v) eluate as light yellowish white crystals.

Physical data of the compounds of Reference Examples 2 to 4 are shown in Table 4.

Reference Example 5-1

4-(4-Benzyl-2-ethyl-3-oxopiperazin-1-yl)-2-trifluoromethylbenzonitrile

A 0.94 ml portion of diisopropylamine was dissolved in 10 ml of anhydrous THF, and the solution was mixed with 4.5 ml of 1.47 M butyl lithium/hexane solution at −20° C., stirred for 10 minutes and then cooled to −78° C. A 20 ml portion of anhydrous THF solution containing 2 g of 4-(4-benzyl-3-oxopiperazin-1-yl)-2-trifluoromethylbenzonitrile synthesized in Reference Example 1-15 was added dropwise thereto, and the mixture was stirred for 20 minutes and then mixed with 0.67 ml of ethyl iodide. After warming up to −10° C., the reaction solution was poured into saturated ammonium chloride aqueous solution and extracted with ethyl acetate, the organic layer was washed and dried, and then the solvent was evaporated under reduced pressure. The residue was purified by a silica gel column chromatography, and 1.5 g of the title compound was obtained from hexane-ethyl acetate (1:1, v/v) eluate as a white foamy substance.

Compounds of Reference Examples 5-2 and 5-3 were synthesized in the same manner as described in Reference Example 5-1.

Reference Example 6-1

4-(4-Benzyl-2-ethylpiperazin-1-yl)-2-trifluoromethylbenzonitrile

At 0° C., 5 ml of 1 M borane-THF solution was added dropwise to 30 ml of anhydrous THF solution containing 1.47 g of 4-(4-benzyl-2-ethyl-3-oxopiperazin-1-yl)-2-trifluoromethylbenzonitrile synthesized in Reference Example 5-1, and the mixture was stirred for 4 hours. After addition of 10 ml of methanol and 38 ml of 1 N hydrochloric acid to the mixture with stirring, the reaction solution was evaporated under reduced pressure, the resulting residue was neutralized with saturated sodium bicarbonate aqueous solution and extracted with ethyl acetate, the organic layer was washed and dried, and then the solvent was evaporated under reduced pressure. The residue was purified by a silica gel column chromatography, and 0.67 g of the title compound was obtained from hexane-ethyl acetate (5:1, v/v) eluate as yellow oily substance.

Compounds of Reference Examples 6-2 and 6-3 were synthesized in the same manner as described in Reference Example 6-1.

Reference Example 7-1

4-(2-Ethylpiperazin-1-yl)-2-trifluoromethylbenzonitrile

A 0.65 g portion of 4-(4-benzyl-2-ethylpiperazin-1-yl)-2-trifluoromethylbenzonitrile synthesized in Reference Example 6-1 and 65 mg of 10% palladium-carbon were stirred in methanol at room temperature for 6 hours at atmospheric pressure in an atmosphere of hydrogen. The insoluble matter was removed by filtration through celite, the filtrate was concentrated under reduced pressure, the resulting residue was purified by a silica gel column chromatography, and 0.46 g of the title compound was obtained from chloroform-methanol-29% aqueous ammonia (10:1:0.1, v/v/v) eluate as a yellow oily substance.

Compounds of Reference Examples 7-2 and 7-3 were synthesized in the same manner as described in Reference Example 7-1.

Structures and physical data of the compounds of Reference Example 5-1 to Reference Example 7-3 are shown in Table 5.

Reference Example 8 trans-4-(2,5-Dimethylpiperazin-1-yl)phthalonitrile

A 1.52 g portion of 4-hydroxyphthalonitrile was dissolved in 30.0 ml of acetonitrile, mixed with 2.1 ml of triethylamine and stirred at −10° C. The reaction solution was mixed with 1.8 ml of anhydrous trifluoromethanesulfonic acid, stirred at 0° C. for 30 minutes and then warmed up to room temperature, mixed with 15 ml of DMF and stirred for 2 hours. After evaporation of the solvent under reduced pressure, the residue was mixed with ethyl acetate and washed with saturated aqueous sodium bicarbonate and then the organic layer was dried over sodium sulfate. After evaporation of the solvent under reduced pressure, the residue was dissolved in 20 ml of acetonitrile and mixed with 2.30 g of 2,5-transmethylpiperazine, and the mixture was heated under reflux for 2 hours and then stirred overnight at room temperature. After evaporation of the solvent under reduced pressure, the residue was mixed with 100 ml of ethyl acetate, washed with saturated aqueous sodium bicarbonate and saturated brine and then dried over sodium sulfate. The title compound was obtained by evaporating the solvent under reduced pressure.

Reference Example 9-1

1-[2-(4-Cyano-3-trifluoromethylanilino)-1,1-dimethylethyl]-3-(4-fluorophenyl)urea 4-(2-Amino-2-methylpropylamino)-2-trifluoromethylbenzonitrile was dissolved in 60 ml of dichloromethane, 0.49 ml of 4-fluorophenyl isocyanate was added dropwise to the solution and then the mixture was stirred at room temperature for 1 hour. The thus precipitated crystals were collected by filtration, washed with dichloromethane and then dried to obtain 1.30 g of the title compound.

The following compound of Reference Example 9-2 was synthesized in the same manner as described in Reference Example 9-1.

1-[4-(4-Cyano-3-trifluoromethylanilino)butyl]-3-(4-fluorophenyl)urea

Reference Example 10

Benzyl 3-methylpiperazine-1-carboxylate

A 4 g portion of 2-methylpiperazine was dissolved in 40 ml of dichloromethane, and 1.71 g of benzyl chloroformate was added dropwise thereto at −78° C. After 1 hour of stirring, the mixture was washed by adding water and dried and then the solvent was evaporated to obtain 2.0 g of the title compound.

Reference Example 11-1

(2S,5R)-4-(2,5-Dimethylpiperazin-1-yl)-2-trifluoromethylbenzonitrile

A 10 g portion of (+/−)-trans-4-(2,5-dimethylpiperazin-1-yl)-2-trifluoromethylbenzonitrile was dissolved in 20 ml of ethanol-water mixed solvent, and fractional recrystallization was repeated using 6.6 g of (−)-dibenzoyl-L-tartaric acid [(−)-DIBETA], thereby obtaining a salt. This salt was added to 5 N aqueous sodium hydroxide, the thus separated oily substance was extracted with ethyl acetate and then the solvent was evaporated to obtain 2 g of the title compound.

Reference Example 11-2

Using (+)-dibenzoyl-D-tartaric acid, (2R,5S)-trans-4-(2,5-dimethylpiperazin-1-yl)-2-trifluoromethylbenzonitrile was obtained by the same procedure of Reference Example 11-1.

Reference Example 12-1

(3S,6R)-1-Benzyl-3,6-dimethylpiperazine-2,5-dione

A 0.98 g portion of N-tert-butoxycarbonyl-L-alanine was added to 50 ml of 0° C.-cooled dichloromethane solution containing 1.07 g of DCC, and the mixture was stirred for 5 minutes. This solution was mixed with 10 ml of dichloromethane solution containing 1.0 g of N-benzyl-D-alanine methyl ester and stirred at room temperature for 2 days. White precipitate was separated by filtration and washed with diethyl ether and then the filtrate was concentrated. The residue was dried under reduced pressure, dissolved with 30 ml of dichloromethane, cooled to 0° C., mixed with 5 ml of trifluoroacetic acid and then stirred at room temperature for 3 hours. The reaction solution was neutralized with saturated aqueous sodium bicarbonate, extracted with chloroform, dried over anhydrous magnesium sulfate, filtered and then concentrated. The residue was subjected to a silica gel column chromatography and purified with n-hexane-ethyl acetate (1:5, v/v) to obtain 1.0 g of the title compound as a colorless oily substance.

Reference Example 12-2

(2R,5S)-1-Benzyl-2,5-dimethylpiperazine

In an atmosphere of argon, 0.57 g of lithium aluminum hydride was added at 0° C. to 30 ml of THF solution containing 1.0 g of (3S,6R)-1-benzyl-3,6-dimethylpiperazine-2,5-dione, and the mixture was stirred overnight with heating under reflux. The reaction mixture was cooled to 0° C., 1.0 ml of water was added dropwise thereto and 1.0 ml of 10% aqueous sodium hydroxide was added dropwise thereto, and then the mixture was further mixed with 1.0 ml of water and stirred for 30 minutes. The precipitate was separated by filtration and washed with ethyl acetate, and the filtrate was washed with 10% aqueous potassium carbonate and saturated brine, dried over anhydrous magnesium sulfate, filtered and then concentrated. The residue was subjected to a silica gel column chromatography and eluted with chloroform-methanol-28% aqueous ammonia (25:1:0.1, v/v/v) to obtain 0.75 g of the title compound as a yellow oily substance.

Reference Example 12-3

(2S,5R)-4-(4-Benzyl-2,5-dimethylpiperazin-1-yl)-2-trifluoromethylbenzonitrile

A 15 ml portion of pyridine solution containing 0.63 g of (2R,5S)-1-benzyl-2,5-dimethylpiperazine was mixed with 0.7 g of 4-fluoro-2-trifluoromethylbenzonitrile and stirred at 90° C. for 2 days. The reaction mixture was concentrated and the residue was purified by a silica gel column chromatography to obtain the title compound from n-hexane-ethyl acetate (9:2, v/v) as a white solid.

Reference Example 12-4

(2S,5R)-4-(2,5-Dimethylpiperazin-1-yl)-2-trifluoromethylbenzonitrile

A 0.92 ml portion of 1-chloroethyl chloroformate was added to 20 ml of dichloroethane solution containing 0.31 g of (2S,5R)-4-(4-benzyl-2,5-dimethylpiperazin-1-yl)-2-trifluoromethylbenzonitrile, and the mixture was stirred for 2 days with heating under reflux. The reaction mixture was concentrated, mixed with 20 ml of methanol and then stirred for 1 day with heating under reflux. The reaction mixture was concentrated and the residue was subjected to a silica gel column chromatography and purified with chloroform-methanol (9:1, v/v) to obtain 0.19 g of the title compound as a yellow oil.

Specific rotation of this compound and its retention time in an optically active HPLC column (CHIRALCEL OD-H, Daicel Chemical Industries) coincided with those of the compound resolved using the (−)-DIBETA of Reference Example 11-1.

Reference Example 13

6-Trifluoromethylnicotinic acid

A 2.9 g portion of 5-cyano-2-trifluoromethylpyridine and 30 ml of concentrated hydrochloric acid were stirred at 90° C. for 13 hours. The reaction mixture was spontaneously cooled to room temperature, mixed with water and then adjusted to pH 2 to 3 with 28% aqueous ammonia. The thus precipitated crystals were collected by filtration and then washed with water to obtain 2.22 g of the title compound.

Reference Example 14

2-Methoxycarbonylisonicotinic acid

A 1.7 ml portion of concentrated sulfuric acid was added to 50 ml of methanol solution containing 5.0 g of pyridine-2,4-dicarboxylic acid, and the mixture was heated under reflux for 1 hour and 10 minutes. After cooling, this was poured into ice water and stirred at 5° C. for 3 hours, and the thus precipitated white solid was collected by filtration. A 5.7 g portion of this product was dissolved in 100 ml of methanol with heating, and the solution was cooled and then stirred at room temperature. By collecting the thus precipitated white solid by filtration, 2.5 g of the title compound was obtained.

Reference Example 15

3-Cyano-6-cyclopropyl-2-oxo-1,2-dihydropyridine-4-carboxylic acid ethyl ester

While stirring at room temperature, 19.2 g of 2-cyanoacetamide was added to 300 ml of ethanol solution containing 41.9 g of 2,4-dioxocyclopropanebutyric acid ethyl ester. After completely dissolving the reagent by warming up to 65° C., 7.4 ml of piperazine was added dropwise to the solution. One hour thereafter, this was cooled to room temperature and stirred for additional 15 hours and 30 minutes. The thus precipitated crystals were collected by filtration and then washed with diethyl ether to obtain 24.1 g of the title compound. This compound was used in the subsequent reaction without further purification.

Reference Example 16

2-Cyclopropyl-6-methoxyisonicotinic acid methyl ester

A 100 ml portion of concentrated hydrochloric acid containing 12.0 g of 3-cyano-6-cyclopropyl-2-oxo-1,2-dihydropyridine-4-carboxylic acid ethyl ester was heated under reflux for 5 hours and 40 minutes. After cooling, the solvent was evaporated to obtain 15.0 g of crude carboxylic acid. A 13.9 g portion of this compound was suspended in 250 ml of benzene, 7.7 ml of methyl iodide and 19.9 g of silver carbonate were added in that order to the suspension with stirring at room temperature, and the mixture was heated to 50° C. After 74 hours, the reaction mixture was cooled to room temperature and filtered through celite and then the solvent was evaporated. The residue was purified by a silica gel column chromatography, and 957 mg of the title compound was obtained from ethyl acetate-hexane (1:6, v/v) eluate.

Reference Example 17

4-Amino-2-bromopyridine

To 450 ml of 67% ethanol aqueous solution were added 8.78 g of 2-bromo-4-nitropyridine N-oxide, 11.2 g of iron powder and 1.2 g of ammonium chloride in that order, and then the mixture was heated under reflux for about 30 minutes. The insoluble matter was removed by filtration, the thus obtained filtrate was evaporated under reduced pressure, and then the thus formed residue was mixed with an appropriate amount of saturated aqueous sodium bicarbonate and extracted with ethyl acetate. The organic layer was washed with water, dried and evaporated under reduced pressure, and then the thus formed crude product was purified by a silica gel column chromatography to obtain 4.4 g of the title compound from chloroform-methanol-28% aqueous ammonia (200:9:1, v/v/v) eluate as light orange crystals.

Reference Example 18

4-Amino-2-(t-butoxycarbonylamino)pyrimidine

A 5.52 g portion of 2,4-diaminopyrimidine was added to 150 ml of t-butanol and dissolved by heating to about 60° C., and the solution was cooled to room temperature, mixed with 12.38 g of DIBOC and then stirred at room temperature for about 3 days. The reaction mixture was evaporated under reduced pressure and the thus formed crude product was purified by a silica gel column chromatography to obtain 7.02 g of the title compound from chloroform-methanol-28% aqueous ammonia (200:9:1, v/v/v) eluate as white crystals.

Reference Example 19

2-Cyano-4-pyridylcarbamic acid t-butyl ester

While stirring at room temperature, 1.8 ml of triethylamine and 2.8 ml of DPPA were added in that order to 100 ml of t-butanol solution containing 1.5 g of 2-cyanoisonicotinic acid, and the mixture was heated under refulx for 4 hours and 25 minutes. The reaction mixture was cooled to room temperature, mixed with water and extracted with ethyl acetate. The organic layer was washed with saturated aqueous sodium bicarbonate and dried over anhydrous sodium sulfate, and then the solvent was evaporated under reduced pressure. The residue was purified by a silica gel column chromatography, and 1.34 g of the title compound was obtained from ethyl acetate-hexane (1:2, v/v) eluate.

Reference Example 20

2-Acetyl-4-pyridylcarbamic acid t-butyl ester

While stirring under ice-cooling, 7.2 ml of methylmagnesium bromide-3 M diethyl ether solution was added to 30 ml of THF solution containing 1.58 g of 2-cyano-4-pyridylcarbamic acid t-butyl ester. This was cooled to room temperature and extracted with ethyl acetate. The organic layer was washed with saturated aqueous sodium bicarbonate and dried over anhydrous sodium sulfate, and then the solvent was evaporated under reduced pressure. The residue was purified by a silica gel column chromatography to obtain the title compound (1.16 g) from ethyl acetate-hexane (1:2, v/v) eluate.

Reference Example 21

5-Aminomethyl-2-methoxypyridine

A 1.00 g portion of 5-cyano-2-methoxypyridine was dissolved in 30 ml of ethanol and 10 ml of 28% aqueous ammonia, mixed with 1 g of Raney nickel and then stirred at room temperature for 4 hours at atmospheric pressure in a stream of hydrogen. After filtration through celite, the solvent was evaporated to obtain 962 mg of the title compound.

Reference Example 22

2-(1-Imidazolyl)pyridine N-oxide

A 0.76 g portion of imidazole was added to 7 ml of N,N-dimethylformamide and mixed with 0.2 g of 90% lithium hydride under ice-cooling and then the mixture was stirred for 40 minutes. Next, 2.17 g of 2-bromopyridine N-oxide hydrochloride was gradually added thereto, the mixture was stirred at room temperature for about 1 hour and further heated at 80° C. for about 1 hour, and then the solvent was evaporated and the thus obtained mixture was subjected to a silica gel column chromatography and eluted with chloroform-methanol-28% aqueous ammonia (10:0.9:0.1, v/v/v) to obtain 1.21 g of the title compound as light yellow crystals.

Reference Example 23

2-(1-Imidazolyl)-4-nitropyridine N-oxide

A 3.22 g portion of 2-(1-imidazolyl)pyridine N-oxide was added to 7.6 g of concentrated sulfuric acid, a mixed solution of 5.2 g of fuming nitric acid and 2.6 g of concentrated sulfuric acid was gradually added dropwise thereto, and then the mixture was heated at 130° C. for about 2.5 hours. The reaction mixture was spontaneously cooled, poured into 150 g of ice-cooled water, neutralized with potassium carbonate and then extracted with 300 ml of ethyl acetate. The organic layer was dried and then concentrated, and the thus obtained mixture was subjected to a silica gel column chromatography and eluted with chloroform-methanol-28% aqueous ammonia (200:0.9:0.1, v/v/v) to obtain 0.12 g of the title compound as yellow crystals.

Reference Example 24

4-Amino-2-(1-imidazolyl)pyridine

A 0.12 g portion of 2-(1-imidazolyl)-4-nitropyridine N-oxide was suspended in 14 ml of 70% ethanol aqueous solution, 0.32 g of iron powder and 20 mg of ammonium chloride were added in that order to the suspension and then the mixture was heated at 100° C. for about 20 minutes. Then, the insoluble matter was immediately removed by filtration, and the resulting filtrate was evaporated under reduced pressure to obtain 0.1 g of the title compound.

Reference Example 25

2-Aminomethyl-6-chloropyridine

A 3.3 g portion of Raney nickel was suspended in 30 ml of ethanol, and the suspension was mixed with 1.42 g of 2-cyano-6-chloropyridine and 10 ml of 28% aqueous ammonia and stirred at room temperature for 4 hours in a stream of hydrogen. The reaction mixture was filtered through celite and the filtrate was concentrated to obtain 1.38 g of the title compound as a mixture.

Reference Example 26

Methyl 2-morpholinoisonicotinate

A 5.0 g portion of 2-chloroisonicotinic acid and 6.91 g of morpholine were suspended in 16 ml of isopropanol and stirred at 150° C. for 27 hours in a sealed tube. The solvent was evaporated and then the residue was mixed with 70 ml of methanol and 5 ml of concentrated sulfuric acid and heated under reflux for 6.5 hours. The solvent was evaporated and the residue was dissolved in chloroform and washed with saturated aqueous sodium bicarbonate. After evaporation of the solvent, the resulting mixture was subjected to a silica gel column chromatography and eluted with hexane-ethyl acetate (4:1, v/v) to obtain 4.42 g of crystals of the title compound.

Reference Example 27

2-Isopropylisonicotinic acid

A 7.5 ml portion of 8 N aqueous potassium hydroxide was added to 50 ml of ethanol solution containing 2.7 g of 4-cyano-2-isopropylpyridine, and the mixture was heated under reflux for 12 hours. After cooling to room temperature, the reaction mixture was mixed with water and diethyl ether and the aqueous layer was separated. The aqueous layer was adjusted to an acidic pH of 3 using 4 N hydrochloric acid and then saturated with sodium chloride. This was extracted with a mixed solvent of ethyl acetate-isopropanol (5:1, v/v) and dried over anhydrous magnesium sulfate, and then the solvent was evaporated under reduced pressure to obtain 3.1 g of the title compound.

Reference Example 28

2-(2,2,2-Trifluoroethoxy)isonicotinic acid

A mixture consisting of 7.5 g of 2-chloroisonicotinic acid, 16 g of potassium tert-butoxide and 100 ml of 2,2,2-trifluoroethanol was stirred at 170° C. for 5 days in a sealed tube. After evaporation of the solvent, the residue was mixed with water and 4 N hydrochloric acid and extracted with chloroform. The solvent was washed with water, dried over anhydrous magnesium sulfate and then concentrated, and the thus formed crystals were washed with hexane to obtain 7.7 g of the title compound.

Reference Example 29

6-Methylaminonicotinic acid

A 20 ml pyridine solution of 10 g of 6-chloronicotinic acid and 27 ml of 40% methylamine aqueous solution was heated at 150° C. for 24 hours in a sealed tube. After spontaneous cooling to room temperature, this was mixed with water and adjusted to pH 3 with 1 N aqueous hydrochloric acid. The precipitated crystals were collected by filtration to obtain 5.82 g of the title compound as grayish white crystals.

Reference Example 30

Synthesis of 6-acetylmethylaminonicotinic acid

A 1.5 g portion of 6-methylaminonicotinic acid in 20 ml of acetic anhydride was heated under reflux for 1.5 hours. After evaporation of the solvent under reduced pressure, the residue was dissolved with saturated aqueous sodium bicarbonate, and the aqueous layer was washed with ethyl acetate and then adjusted to pH 3 using concentrated hydrochloric acid. Then the aqueous layer was extracted with chloroform, the organic layer was washed and dried, and then the solvent was evaporated under reduced pressure to obtain 280 mg of the title compound as white crystals.

Reference Example 31-1

Methyl 2-isopropoxyisonicotinate

A mixture of 5 g of 6-chloronicotinic acid, 6.5 g of sodium isopropoxide and 100 ml of isopropanol was stirred at 150° C. for 4 days in a sealed tube. After evaporation of the solvent, the residue was mixed with 200 ml of methanol and 5 ml of concentrated sulfuric acid and heated under reflux for 15 hours. After concentration of the solvent, the residue was mixed with chloroform and washed with saturated aqueous sodium bicarbonate. After evaporation of the solvent, the resulting mixture was subjected to a silica gel column chromatography and eluted with hexane-ethyl acetate (10:1, v/v) to obtain 2.5 g of crystals of the title compound.

Compound of Reference Example 31-2 was synthesized in the same manner as described in Reference Example 31-1.
Methyl 2-(2-morpholinoethoxy)isonicotinate

Reference Example 32-1 trans-4-(2,5-Dimethylpiperazin-1-yl)-2-methoxybenzonitrile

A 1.35 g portion of potassium tert-butoxide and 0.48 ml of methanol were added to 5 ml of THF, and the mixture was stirred for 30 minutes. Next, this was mixed with 934 mg of trans-4-(2,5-dimethylpiperazin-1-yl)-2-fluorobenzonitrile synthesized in Reference Example 14 and stirred at room temperature for 2 days. This was mixed with saturated brine and extracted with ethyl acetate, the organic layer was washed with water, and then the solvent was evaporated and the resulting mixture was subjected to a silica gel column chromatography and eluted with ethyl acetate-methanol-28% aqueous ammonia (9:1:0.1, v/v/v) to obtain 900 mg of the title compound.

Compounds of Reference Examples 32-2 and 32-3 were synthesized in the same manner as described in Reference Example 32-1.

Reference Example 32-2 trans-4-(2,5-Dimethylpiperazin-1-yl)-2-(2-methoxyethoxy)benzonitrile

Reference Example 32-3 trans-4-(2,5-Dimethylpiperazin-1-yl)-2-(2-morpholinoethoxy)benzonitrile

Physical data of the compounds of Reference Examples 8 to 32 are shown in Table 6.

Structures and physical data of the compounds of reference examples are shown in the following tables.

In this connection, each symbol in the tables means as follows.

Ref. No.: Reference Example No.
DATA: Physical data

NMR: Nuclear magnetic resonance spectrum (measured in DMSO-d$_6$, TMS was used as an internal standard unless otherwise noted)
MS: Mass spectrometry data
Me: Methyl
Et: Ethyl
Ph: Phenyl Remarks: Configuration of compounds having R$^2$ and R$^3$ (the case of no particular description indicates a racemate or a compound having no stereo isomer), or show a salt of a compound which formed the salt.

TABLE 1

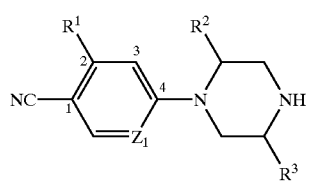

| Ref. No. | R$^1$ | Z$_1$ | R$^2$ | R$^3$ | DATA | Remarks |
|---|---|---|---|---|---|---|
| 1-1 | 2-CF3 | CH | Me | Me | NMR(CDCl3)δ: 1.20(6H, d, J=7), 2.72(1H, dd, J=5, 13), 3.02–3.16(1H, m), 3.26–3.49(3H, m), 3.70–3.82(1H, m), 4.01–4.14(1H, m), 6.96(1H, dd, J=2, 9), 7.11(1H, d, J=2), 7.62(1H, d, J=9) | trans |
| 1-2 | 2-CF3 | CH | H | H | NMR: δ: 2.41(1H, br), 2.78–2.83(4H, m), 3.33–3.38(4H, m), 7.21(1H, dd, J=2, 7), 7.27(1H, d, J=2), 7.81(1H, d, J=7) | |
| 1-3 | H | CH | Me | Me | NMR(CDCl3)δ: 1.11(3H, d, J=6), 1.16(3H, d, J=7), 2.69(1H, dd, J=6, 13), 2.90(1H, dd, J=6, 12), 3.17–3.31(3H, m), 3.49–3.59(1H, m), 7.49–7.54(2H, m), 7.65–7.72(2H, m) | trans |
| 1-4 | 2-F | CH | Me | Me | NMR(CDCl3)δ: 1.20(6H, d, J=6), 2.70(1H, dd, J=5, 13), 3.03–3.12(1H, m), 3.24–3.36(3H, m), 3.65–3.76(1H, m), 6.54(1H, dd, J=2, 13), 6.62(1H, d, J=2, 9), 7.39(1H, dd, J=8, 9) | trans |
| 1-5 | 2-Cl | CH | Me | Me | NMR(CDCl3)δ: 1.17–1.21(6H, m), 2.66–2.72(1H, m), 3.02–3.07(1H, m), 3.23–3.34(3H, m), 3.66–3.71(1H, m), 6.72–6.76(1H, m), 6.87(1H, d, J=2), 7.45(1H, d, J=9) | trans |
| 1-6 | 2-Br | CH | Me | Me | NMR(CDCl3)δ: 1.18(3H, d, J=6), 1.19(3H, d, J=7), 2.69(1H, dd, J=5, 13), 2.99–3.08(1H, m), 3.23–3.35(3H, m), 3.61–3.74(1H, m), 6.79(1H, dd, J=2, 9), 7.05(1H, d, J=2), 7.45(1H, d, J=9) | trans |
| 1-7 | 2-Me | CH | Me | Me | NMR: δ: 1.06(6H, d, J=6), 2.37(3H, s), 2.46–2.53(1H, m), 3.05–3.21(4H, m), 3.70–3.81(1H, m), 6.75–6.81(1H, m), 6.83–6.87(1H, m), 7.47(1H, d, J=8) | trans |
| 1-8 | 3-F | CH | Me | Me | NMR(CDCl3)δ: 0.96(3H, d, J=6), 1.07(3H, d, J=7), 2.40(1H, dd, J=10, 11), 2.72(1H, dd, J=10, 12), 3.01–3.22(4H, m), 7.12–7.17(1H, m), 7.32(1H, dd, J=2, 11), 7.38–7.41(1H, m) | trans |
| 1-9 | 3-CF3 | CH | Me | Me | NMR(CDCl3)δ: 0.75(3H, d, J=6), 1.02(3H, d, J=6), 2.24–2.31(1H, m), 2.73(1H, dd, J=11, 12), 2.91(1H, dd, J=3, 11), 2.98–3.09(3H, m), 7.52(1H, d, J=8), 7.81–7.83(1H, m), 7.95–7.97(1H, m) | trans |
| 1-10 | 2-CF3 | CH | H | Me | NMR: δ: 1.03(3H, d, J=6), 2.37–2.47(1H, m), 2.63–2.84(3H, m), 2.91–2.99(1H, m), 3.80–3.92(2H, m), 7.21(1H, dd, J=2, 9), 7.25–7.29(1H, m), 7.79(1H, d, J=9) | |
| 1-11 | H | N | Me | Me | NMR(CDCl3)δ: 1.19(3H, d, J=7), 1.27(3H, d, J=7), 1.56(1H, br), 2.68(1H, dd, J=3, 13), 3.28–3.41 (5H, m), 3.90–3.97(1H, m), 4.33–4.41(1H, m), 6.53(1H, d, J=9), 7.58(1H, dd, J=2, 9), 8.02(1H, br), 8.39(1H, d, J=2) | trans |

TABLE 2

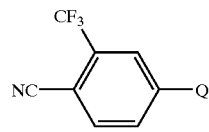

| Ref. No. | Q | DATA | Remarks |
|---|---|---|---|
| 1-12 | —N⌒NH (diazepane) | NMR: δ: 1.69–1.77(2H, m), 2.29(1H, br), 2.61–2.66(2H, m), 2.82–2.87(2H, m), 3.55–3.60(2H, m), 3.62–3.68(2H, m), 7.00–7.05(2H, m), 7.74(1H, d, J=8) | |
| 1-13 | MeNH-CH$_2$-C(Me)$_2$-NH$_2$ | NMR: δ: 1.06(6H, s), 1.51(2H, br), 3.02(2H, d, J=6), 6.90–6.97(1H, m), 7.04–7.11 (1H, m), 7.15(1H, br), 7.68(1H, d, J=9) | |
| 1-14 | MeNH-(CH$_2$)$_4$-NH$_2$ | NMR: δ: 1.36(2H, br), 1.38–1.47(2H, m), 1.52–1.62(2H, m), 2.53–2.60(2H, m), 3.09–3.18(2H, m), 6.80–6.84(1H, m), 7.01(1H, br), 7.26–7.34(1H, m), 7.70(1H, d, J=9) | |

TABLE 2-continued

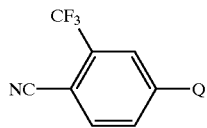

| Ref. No. | Q | DATA | Remarks |
|---|---|---|---|
| 1-15 | (N-methyl-N'-benzyl-piperazinone) | NMR: δ: 3.37–3.44(2H, m), 3.69–2.76(2H, m), 4.17(2H, s), 4.62(2H, s), 7.20(1H, dd, J=2, 9), 7.25–7.39(6H, m), 7.86(1H, d, J=9) | |
| 1-16 | 2,6-dimethyl-N-methylpiperazine | NMR: δ: 1.03(6H, d, J=6), 2.24–2.39(2H, m), 2.67–2.82(2H, m), 3.83–3.93(2H, m), 7.27–7.31(1H, m), 7.80(1H, d, J=9) | cis |

TABLE 3

| Ref. No. | Structure | DATA | Remarks |
|---|---|---|---|
| 1-17 | F₃C, Me, O₂N-phenyl-piperazine-Me | NMR(CDCl3) δ: 1.20–1.25(6H, m), 2.74(1H, dd, J=4, J=13), 3.18(1H, dd, J=4, J=12), 3.29–3.43(3H, m), 3.76–3.87(1H, m), 6.93(1H, dd, J=3, J=9), 7.14(1H, d, J=3), 8.02(1H, d, J=9) | trans |

TABLE 4

| Ref. No. | DATA |
|---|---|
| 2 | NMR: δ :0.92(3H, d, J=6), 1.39(9H, s), 2.13–2.35(1H, m), 2.43–2.55(2H, m), 2.74–2.83(1H, m), 3.65–3.78(2H, m) |
| 3 | NMR: δ :1.05(3H, d, J=7), 1.42(9H, s), 2.93–3.25(3H, m), 3.68–3.81(2H, m), 3.84–3.99(1H, br), 4.23–4.36(1H, br), 7.15–7.21(1H, m), 7.22–7.27(1H, m), 7.83–7.87(1H, m) |
| 4 | NMR: δ :1.12(3H, d, J=6), 2.30–2.50(1H, br), 2.60–2.70(1H, m), 2.78–2.88(2H, m), 2.93–3.03(2H, m), 3.58–3.65(1H, m), 4.12–4.21(1H, m), 7.14–7.19(1H, m), 7.22(1H, d, J=2), 7.81(1H, d, J=9) |

TABLE 5

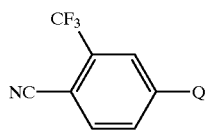

| Ref. No. | Q | DATA |
|---|---|---|
| 5-1 | Et-piperazinone-N-Me, N'-Bn | NMR: δ: 0.95(3H, t, J=7), 1.88–1.98(2H, m), 3.33–3.39(1H, m), 3.41–3.50(1H, m), 3.52–3.62(1H, m), 3.93(1H, dt, J=5, 13), 4.50(1H, d, J=15), 4.56(1H, t, J=7), 4.67(1H, d, J=15), 7.19–7.28(5H, m), 7.29–7.38(2H, m), 7.81(1H, d, J=8) |

TABLE 5-continued

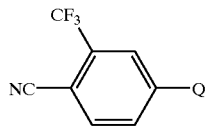

| Ref. No. | Q | DATA |
|---|---|---|
| 5-2 | (3-isopropyl-1-methyl-4-benzyl-piperazin-2-one) | NMR: δ: 0.97(3H, d, J=6), 1.07(3H, d, J=6), 2.19–2.33(1H, m), 3.43–3.50(2H, m), 3.59–3.69(1H, m), 3.76–3.86(1H, m), 4.36(1H, d, J=7), 4.43(1H, d, J=15), 4.71(1H, d, J=15), 7.21–7.28(5H, m), 7.28–7.38(2H, m), 7.81(1H, d, J=8) |
| 5-3 | (3,3-dimethyl-1-methyl-4-benzyl-piperazin-2-one) | NMR: δ: 1.52(6H, s), 3.34–3.39(2H, m), 3.55–3.61(2H, m), 4.59(2H, s), 7.24–7.41(5H, m), 7.46–7.52(2H, m), 7.94(1H, d, J=8) |
| 6-1 | (3-ethyl-1-methyl-4-benzyl-piperazine) | NMR: δ: 0.72(3H, t, J=7), 1.41–1.56(1H, m), 1.77–1.90(1H, m), 2.04–2.16(2H, m), 2.82(1H, d, J=11), 2.86–2.95(1H, m), 3.14(1H, dt, J=3, 13), 3.40(1H, d, J=13), 3.60(1H, d, J=13), 3.74–3.83(1H, m), 3.99–4.07 (1H, m), 7.13–7.18(1H, m), 7.20–7.22(1H, m), 7.23–7.31(1H, m), 7.32–7.36(4H, m), 7.79(1H, d, J=9) |
| 6-2 | (3-isopropyl-1-methyl-4-benzyl-piperazine) | NMR: δ: 0.66(3H, d, J=7), 0.81(3H, d, J=7), 1.93–2.00(1H, m), 2.01–2.11(1H, m), 2.50–2.61(1H, m), 2.82–2.94(2H, m), 3.17–3.28(1H, m), 3.35(1H, d, J=13), 3.57(1H, d, J=13), 3.77–3.91(2H, m), 7.15–7.22(2H, m), 7.24–7.30(1H, m), 7.30–7.35(4H, m), 7.73(1H, d, J=9) |
| 6-3 | (3,3-dimethyl-1-methyl-4-benzyl-piperazine) | NMR: δ: 1.17(6H, s), 2.30(2H, s), 2.49–2.54(2H, m), 3.26–3.31(2H, m), 3.51(2H, s), 7.23–7.35(5H, m), 7.46–7.51(2H, m), 7.95(1H, d, J=9) |
| 7-1 | (3-ethyl-1-methyl-piperazine) | NMR: δ: 0.83(3H, t, J=7), 1.41–1.56(1H, m), 1.75–1.92(1H, m), 2.37–2.50(1H, br), 2.57–2.76(2H, m), 2.90–3.05(3H, m), 3.60–3.69(1H, m), 3.84–3.93(1H, m), 7.12–7.21(2H, m), 7.77(1H, d, J=9) |
| 7-2 | (3-isopropyl-1-methyl-piperazine) | NMR: δ: 0.68(3H, d, J=7), 0.97(3H, d, J=7), 2.26–2.44(1H, br), 2.52–2.66(3H, m), 2.84–2.92(1H, m), 3.00–3.14(2H, m), 3.63–3.77(2H, m), 7.12–7.19(2H, m), 7.71(1H, d, J=9) |
| 7-3 | (3,3-dimethyl-1-methyl-piperazine) | NMR: δ: 1.16(6H, s), 2.61(2H, s), 2.80–2.86(2H, m), 3.12–3.19(2H, m), 3.25–3.39(1H, br), 7.42–7.47(2H, m), 7.92(1H, d, J=9) |

TABLE 6

| Ref. No. | DATA |
|---|---|
| 8 | NMR(CDCl3) δ: 1.20–1.24(6H, m), 2.72(1H, dd, J=4, 13), 3.11–3.19(1H, m), 3.29–3.40(3H, m), 3.72–3.82(1H, m), 6.99(1H, dd, J=3, 9), 7.09(1H, d, J=3), 7.56(1H, d, J=9) |
| 9-1 | NMR: δ: 1.28(6H, s), 3.46–3.57(2H, m), 6.93–6.97(1H, m), 7.04(2H, dd, J=9, 9), 7.16–7.25(2H, m), 7.31–7.37(1H, m), 7.64(1H, d, J=8), 8.32(1H, br) |
| 9-2 | NMR: δ: 1.47–1.64(4H, m), 3.09–3.19(4H, m), 6.15–6.21(1H, m), 6.81–6.86(1H, m), 7.01(1H, br), 7.04(2H, dd, J=9, 9), 7.24–7.29(1H, m), 7.36–7.42 (2H, m), 7.69(1H, d, J=8), 8.51(1H, br) |
| 10 | NMR(CDCl3) δ: 1.05(3H, d, J=6), 1.51(1H, br), 2.47(1H, br), 2.65–3.02(4H, m), 4.03(1H, br), 5.08–5.18(2H, m), 7.24–7.38(5H, m) |
| 11-1 | MS(FAB) 284[M+ H]+; [α]$_D$25=+100.6(c=1.018, EtOH) |
| 11-2 | MS(FAB) 284[M+ H]+; [α]$_D$25=+97.04(c=1.014, EtOH) |
| 12-1 | NMR(CDCl3): 1.42(3H, d, J=7), 1.54(3H, d, J=7), 3.86(1H, q, J=7), 4.09(1H, d, J=15), 4.14(1H, q, J=7), 5.17(1H, d, J=15), 6.98(1H, br s), 7.22–7.36(5H, m); [α]$_D$25=−17.15(c=1.0, CDCl3) |
| 12-2 | NMR(CDCl3): 0.94(3H, d, J=6), 1.14(3H, d, J=6), 1.49(1H, br s), 1.63(1H, dd, J=10, 11), 2.17–2.28(1H, m), 2.60–2.70(2H, m), 2.74–2.83(1H, m), 2.91(1H, dd, J=3, 12), 3.09(1H, d, J=14), 4.10(1H, d, J=14), 7.22–7.32(5H, m); [α]$_D$25=−133.5(c=1.0, CDCl3) |
| 12-3 | NMR(CDCl3): 1.08(3H, d, J=7), 1.24(3H, d, J=7), 2.46(1H, dd, J=2, 6), 2.89(1H, dd, J=4, 12), 3.15(1H, m), 3.37(1H, d, J=12), 3.48(1H, dd, J=3, 12), 3.57(1H, d, J=14), 3.67(1H, d, J=14), 4.00(1H, m), 6.89(1H, dd, J=3, 9), 7.06(1H, d, J=3), 7.29–7.39(5H, m), 7.58(1H, d, J=9) |
| 13 | NMR: 8.03–8.09(1H, m), 8.51–8.58(1H, m), 9.20–9.24 (1H, m), 13.91(1H, br s) |
| 14 | NMR: 3.92(3H, s), 8.06(1H, dd, J=2, 5), 8.38–8.40(1H, m), 8.92(1H, dd, J=1, 5) |
| 15 | MS(FAB) (m/z): 233[(M+H)+] |
| 16 | NMR(CDCl3): 0.09–1.11(4H, m), 1.95–2.07(1H, m), 3.89 (3H, s), 3.92(3H, s), 7.01(1H, d, J=1), 7.29(1H, d, J=1) |
| 17 | NMR: 6.36(2H, br s), 6.44(1H, dd, J=2, 6), 6.63(1H, d, J=2), 7.74(1H, d, J=6) |
| 18 | NMR: 1.43(9H, s), 6.07(1H, d, J=6), 6.69(2H, br s), 7.86(2H, d, J=6), 9.20(1H, s) |
| 19 | NMR: 1.50(9H, s), 7.66(1H, d, J=3), 7.91–7.96(1H, m), 8.47–8.56(1H, m), 10.24—10.33(1H, m) |
| 20 | NMR(CDCl3): 1.54(9H, s), 2.71(3H, s), 6.85–6.98(1H, m), 7.75–7.82(2H, m), 8.49–8.55(1H, m) |
| 21 | NMR(CDCl3): 1.30–1.55(2H, m), 3.84(1H, br s), 3.93(3H, s), 6.78(1H, d, J=8), 7.53–7.62(1H, m), 8.05–8.11(1H, m) |
| 22 | MS(FAB) m/z 162[(M+H)+] |
| 23 | MS(FAB) m/z 207[(M+H)+] |
| 24 | MS(FAB) m/z 161[(M+H)+] |
| 25 | MS(EI) m/z 142[M+] |
| 26 | MS(FAB) m/z 223[(M+H)+] |
| 27 | NMR: 1.26(6H, d, J=7), 3.06–3.30(1H, m), 7.63(1H, dd, J=2, 5), 7.68–7.71(1H, m), 8.68(1H, dd, J=1, 5), 13.6(1H, br s) |
| 28 | NMR(CDCl3): 4.80(2H, q, J=9), 7.46–7.51(1H, m), 7.56(1H, dd, J=1, 5), 8.26(1H, dd, J=1, 6) |
| 29 | MS(FAB) m/z 153[(M+H)+] |
| 30 | MS(FAB) m/z 195[(M+H)+] |
| 31-1 | MS(FAB) m/z 196[(M+H)+] |
| 31-2 | MS(FAB) m/z 267[(M+H)+] |
| 32-1 | NMR(CDCl3) δ: 1.12(3H, d, J=6), 1.17(3H, d, J=7), 1.54 (1H, br), 2.69(1H, dd, J=6, 13), 2.88(1H, dd, J=6, 12), 3.15–3.34(3H, m), 3.48–3.57(1H, m), 3.90(3H, s), 6.41 (1H, d, J=2), 6.52(1H, dd, J=2, 8), 7.39(1H, d, J=8) |
| 32-2 | MS(FAB) m/z 290[(M+H)+] |
| 32-3 | MS(FAB) m/z 345[(M+H)+] |

Example 1-1 trans-4-(4-Cyano-3-trifluoromethylphenyl)-4'-fluoro-2,5-dimethylpiperazine-1-carboxanilide A 300 mg portion of trans-4-(2,5-dimethylpiperazin-1-yl)-2-trifluoromethylbenzonitrile synthesized in Reference Example 1-1 was dissolved in 10 ml of dichloromethane, 0.13 ml of p-fluoro benzisocyanate was added dropwise to the solution under ice-cooling, and the mixture was stirred at room temperature for 1 hour. The reaction mixture was washed with water, the solvent was evaporated and then the resulting residue was purified by a silica gel column chromatography to obtain 390 mg of the title compound from chloroform-methanol (99:1, v/v) eluate as colorless oil. Thereafter, this was crystallized from acetone-diisopropyl ether to obtain it as 165 mg of colorless crystals.

Compounds of Examples 1-2 to 1-56 were synthesized in the same manner as described in Example 1-1.

Example 2-1 trans-4-(4-Cyano-3-trifluoromethylphenyl)-2,5-dimethyl-N-(2-thienyl)piperazine-1-carboxamide A 0.32 ml portion of 2-thenoyl chloride was dissolved in 10 ml of acetonitrile to which were subsequently added 0.49 ml of triethylamine and then 290 mg of sodium azide under ice-cooling, and the mixture was stirred at room temperature for 3 hours. The reaction mixtrue was poured into ice water and extracted with diethyl ether. The organic layer was washed with saturated brine and dried over magnesium sulfate. By evaporating the solvent under reduced pressure, light brown crystals were obtained.

The thus obtained crystals were dissolved in 10 ml of toluene and stirred at 100° C. for 3 hours. The reaction mixture was spontaneously cooled, mixed with 10 ml of acetonitrile and the with 450 mg of trans-4-(2,5-dimethylpiperazin-1-yl)-2-trifluoromethylbenzonitrile synthesized in Reference Example 1-1, and the mixture was stirred for 20 minutes. After evaporation of the solvent under reduced pressure, the residue was dissolved in ethyl acetate, washed with saturated sodium bicarbonate solution, water and saturated brine in that order and then dried over sodium sulfate. The solvent was evaporated under reduced pressure and the residue was purified by a silica gel column chromatography to obtain 504 mg of the light yellow title compound from ethyl acetate-hexane (1:1, v/v) eluate.

Compounds of Examples 2-2 to 2-10 were synthesized in the same manner as described in Example 2-1.

Example 3-1 trans-4-(4-Cyano-3-trifluoromethylphenyl)-2,5-dimethyl-N-phenethylpiperazine-1-carboxamide A 5 ml portion of acetonitrile, 0.17 ml of triethylamine and 0.26 ml of DPPA were added to 180 mg of hydrocinnamic acid and heated under reflux for 1.5 hours. The reaction mixture was spontaneously cooled, mixed with 280 mg of trans-4-(2,5-dimethylpiperazin-1-yl)-2-trifluoromethylbenzonitrile synthesized in Reference Example 1-1 and stirred at room temperature for 1 hour. The solvent was evaporated under reduced pressure and the residue was purified by a silica gel column chromatography to obtain 204 mg of the title compound from ethyl acetate-chloroform (2:1, v/v) eluate as colorless oil.

Compounds of Examples 3-2 to 3-4 were synthesized in the same manner as described in Example 3-1.

Example 4 trans-2',4'-Dibromo-4-(4-cyano-3-fluorophenyl)-2,5-dimethylpiperazine-1-carboxanilide A 300 mg portion of 2,4-dibromoaniline was dissolved in 10 ml of THF, and the solution was mixed with 153 mg of triphosgene under ice-cooling and then stirred at room temperature for 4 hours. Next, to this was added dropwise 5 ml of THF solution containing 427 mg of trans-4-(2,5-dimethylpiperazin-1-yl)-2-fluorobenzonitrile synthesized in Reference Example 1-1 and 460 mg of triethylamine, and the mixture was further stirred for 1 hour. After evaporation of the solvent, the thus obtained residue was dissolved in ethyl acetate, washed with saturated sodium bicarbonate solution and saturated brine in that order and then dried over sodium sulfate. After evaporation of the solvent under reduced pressure, the residue was purified by a silica gel column chromatography to obtain 390 mg of the title compound from chloroform-hexane (1:1, v/v) eluate as a light yellow product.

Example 5-1 trans-4-(4-Cyano-3-trifluoromethylphenyl)-2,5-dimethyl-N-(1-methyl-1-phenylethyl)piperazine-1-carboxamide A 532 mg portion of DIBOC was dissolved in 10 ml of acetonitrile, 3 ml of acetonitrile containing 124 mg of DMAP and 235 mg of cumylamine was added dropwise to the solution, and then the mixture was stirred at room temperature for 10 minutes. Next, this was mixed with 300 mg of trans-4-(2,5-dimethylpiperazin-1-yl)-2-trifluoromethylbenzonitrile synthesized in Reference Example 1-1 and stirred at room temperature for 5 hours. The solvent was evaporated under reduced pressure, and the thus obtained residue was dissolved in ethyl acetate, washed with saturated sodium bicarbonate solution and saturated brine in that order and then dried over sodium sulfate. The solvent was evaporated under reduced pressure and the residue was purified by a silica gel column chromatography to obtain 475 mg of the title compound from ethyl acetate-hexane (1:1, v/v) eluate.

Compounds of Examples 5-2 and 5-3 were synthesized in the same manner as described in Example 5-1.

Example 6-1

(2R,5S)-N-(2-Bromo-4-pyridyl)-4-(4-cyano-3-trifluoromethylphenyl)-2,5-dimethylpiperazine-1-carboxamide A 1.66 g portion of 4-amino-2-bromopyridine was dissolved in 1.4 ml of pyridine, mixed with 2.0 g of phenyl chloroformate and stirred at room temperature for 4 days. Next, this was mixed with 2 g of (2S,5R)-4-(2,5-dimethylpiperazin-1-yl)-2-trifluoromethylbenzonitrile synthesized in Reference Example 11-1 and heated at 100° C. for 1 hour and 30 minutes. After evaporation of the solvent, the residue was dissolved in ethyl acetate, washed with water and then with saturated brine and dried over magnesium sulfate. After evaporation of the solvent, the residue was subjected to a silica gel column chromatography and eluted with chloroform-methanol (30:1, v/v), and the resulting fraction was subjected to crystallization from ethyl acetate-hexane to obtain 2.7 g of the title compound.

NMR: 1.10 (3H, d, J=6), 1.20 (3H, d, J=6), 3.35–3.52 (2H, m), 3.68–3.80 (1H, m), 3.82–3.96 (1H, m), 4.28–4.60 (2H, m), 7.22–7.35 (2H, m), 7.50–7.58 (1H, m), 7.80–7.90 (2H, m), 8.14 (1H, d, J=5), 9.19 (1H, s) Compounds of Examples 6-2 to 6-16 were synthesized in the same manner as described in Example 6-1.

Example 6-13

(2R,5S)-4-(4-Cyano-3-trifluoromethylphenyl)-N-(6-methoxy-3-pyridyl)-2,5-dimethylpiperazine-1-carboxamide NMR: 1.11 (3H, d, J=7), 1.18 (3H, d, J=7), 3.30–3.45 (2H, m), 3.70–3.76 (1H, m), 3.80 (3H, s), 3.84–3.90 (1H, m), 4.36–4.45 (2H, m), 6.75 (1H, d, J=9), 7.24–7.33 (2H, m), 7.27 (1H, dd, J=3, 9), 7.85 (1H, d, J=9), 8.19 (1H, d, J=3), 8.56 (1H, s)

Example 7-1

(2R,5S)-4-(4-Cyano-3-trifluoromethylphenyl)-N-[(6-methoxy-3-pyridyl)methyl]-2,5-dimethylpiperazine-1-carboxamide Under ice-cooling, 10 ml of dichloromethane solution containing 700 mg of (2S,5R)-trans-4-(2,5-dimethylpiperazin-1-yl)-2-trifluoromethylbenzonitrile and 274 mg of triethylamine was added to 10 ml of dichloromethane solution containing 252 mg of triphosgene and stirred for 1 hour. To this was added dropwise 10 ml of dichloromethane solution containing 409 mg of 5-aminomethyl-2-methoxypyridine synthesized in Reference Example and 274 g of triethylamine, and the mixture was stirred overnight at room temperature. The solvent was evaporated, the thus obtained residue was mixed with water, extracted with ethyl acetate and dried, and then the solvent was evaporated. The resulting residue was subjected to a silica gel column chromatography and eluted with chloroform-methanol (50:1, v/v) to obtain 1.02 g of the title compound.

Compounds of Examples 7-2 to 7-11 were synthesized in the same manner.

Example 8-1

3-(4-Cyano-3-trifluoromethylphenyl)-N-(4-fluorophenyl)-5,5-dimethyl-1-imidazolidinecarboxamide A 1.0 g portion of 1-[2-(4-cyano-3-trifluoromethylanilino)-1,1-dimethylethyl]-3-(4-fluorophenyl)urea synthesized in Reference Example 9-1 was dissolved in 10 ml of acetic acid, and the solution was mixed with 0.4 ml of formalin and heated at 50° C. for 2 hours. The solvent was evaporated, the resulting residue was purified by a silica gel column chromatography, and the compound obtained from chloroform-methanol (30:1, v/v) eluate was washed with diisopropyl ether to obtain 751 mg of the title compound.

Compound of Example 8-2 was synthesized in the same manner as described in Example 8-1.

Example 9 trans-4-(4-Cyano-3-trifluoromethylphenyl)-N-(4-fluorophenyl)-2,5-dimethylpiperazine-1-sulfonamide A 1.21 g portion of trans-4-(2,5-dimethylpiperazin-1-yl)-2-trifluoromethylbenzonitrile synthesized in Reference Example 1-1 and 2.05 g of sulfamide were heated under reflux for 1.5 hours in 15 ml of pyridine. Next, this was mixed with 4.05 ml of 4-fluoroaniline and again heated under reflux for 4 hours. After evaporation of the solvent, the residue was purified by a silica gel column chromatography to obtain 701 mg of the title compound from toluene-ethyl acetate eluate.

Example 10 trans-4'-Amino-4-(4-cyano-3-trifluoromethylphenyl)-2,5-dimethylpiperazine-1-carboxanilide A 450 mg portion of trans-4-(4-cyano-3-trifluoromethylphenyl)-2,5-dimethyl-4'-nitropiperazine-1- carboxanilide synthesized in Example 1-4 was dissolved in 8 ml of methanol, and the solution was mixed with 4 ml of water, 280 mg of iron powder and 30 mg of ammonium chloride and heated under reflux for 5 hours. The reaction solution was again mixed with 280 mg of iron powder and 30 mg of ammonium chloride and further heated under reflux for 2 hours. The reaction solution was filtered through celite, and the solvent in the filtrate was evaporated under reduced pressure. The residue was dissolved in ethyl acetate, washed with water and saturated brine in that order and then dried over sodium sulfate. The solvent was evaporated under reduced pressure, and the residue was purified by a silica gel column chromatography (methanol-chloroform) to obtain 260 mg of the title compound as colorless crystals.

Example 11 trans-4'-Acetamino-4-(4-cyano-3-trifluoromethylphenyl)-2,5-dimethylpiperazine-1-carboxyanilide A 300 mg portion of trans-4'-amino-4-(4-cyano-3-trifluoromethylphenyl)-2,5-dimethylpiperazine-1-carboxyanilide synthesized in Example 10 and 88 mg of acetic anhydride were dissolved in 10 ml of dichloroethane and stirred at room temperature for 10 hours. After evaporation of the solvent, the residue was dissolved in ethyl acetate, washed with water and saturated brine and then dried over sodium sulfate. The solvent was evaporated under reduced pressure, and the residue was crystallized from ethyl acetate-hexane to obtain 195 mg of the title compound as colorless crystals.

Example 12-1

(2R,5S)-4-{[4-(4-Cyano-3-trifluoromethylphenyl)-2,5-dimethylpiperazine-1-carbonyl]amino}pyridine-2-carboxylic acid A 40 ml portion of 1 N sodium hydroxide aqueous solution was added dropwise to 40 ml of THF solution containing 3.36 g of ethyl (2R,5S)-4-{[4-(4-cyano-3-trifluoromethylphenyl)-2,5-dimethylpiperazine-1-carbonyl]amino}pyridine-2-carboxylate synthesized in Example 18-3, and the mixture was stirred at room temperature for 1 hour. This was adjusted to pH 2 to 3 by adding 4 N hydrochloric acid under ice-cooling, and the thus formed precipitate was collected by filtration, washed with purified water and then dried at 70° C. under reduced pressure to obtain 2.80 g of the title compound.

Compounds of Examples 12-2 and 12-3 were synthesized in the same manner.

Example 13-1

(2R,5S)-4-(4-Cyano-3-trifluoromethylphenyl)-2,5-dimethyl-N-(2-methylcarbamoyl-4-pyridyl)piperazine-1-carboxamide Under ice-cooling, 332 mg of HOBT and 519 mg of WSC were added in that order to a suspension of 1.10 g of (2R,5S)-4-{[4-(4-cyano-3-trifluoromethylphenyl)-2,5-dimethylpiperazine-1-carbonyl]amino}pyridine-2-carboxylic acid synthesized in Example 12-1 in 30 ml of DMF, and then the mixture was warmed up to room temperature and stirred for 1.5 hours. This was again ice-cooled, 10 ml of 40% aqueous methylamine was added thereto in one portion and then the mixture was stirred overnight. This was mixed with purified water and extracted with ethyl acetate, and the thus obtained organic layer was washed twice with saturated brine, dried over anhydrous magnesium sulfate and then concentrated. The residue was subjected to a silica gel column chromatography to obtain 674 mg of the title compound from methanol-ethyl acetate (1:9, v/v) eluate.

NMR: 1.10 (3H, d, J=6), 1.21 (3H, d, J=6), 2.81 (3H, d, J=5), 3.40 (1H, dd, J=4, 13), 3.46 (1H, br d, J=11), 3.75 (1H, dd, J=2, 13), 3.96 (1H, br d, J=14), 4.33–4.43 (1H, m), 4.49–4.60 (1H, m), 7.27 (1H, dd, J=2, 9), 7.31 (1H, d, J=2), 7.83 (1H, dd, J=2, 5), 7.85 (1H, d, J=9), 8.17 (1H, d, J=2), 8.38 (1H, d, J=5), 8.69 (1H, dd, J=5), 9.23 (1H, s)

Compounds of Examples 13-2 to 13-4 were synthesized in the same manner.

Example 14 trans-$^4$-(4-Cyano-3-trifluoromethylphenyl)-2,5-dimethyl-4'-(methylamino)sulfonylpiperazine-1-carboxyanilide A 200 mg portion of $_4$-chlorosulfonylphenyl isocyanate was dissolved in 20 ml of dichloromethane, 5 ml of dichloromethane containing 400 mg of trans-$^4$-(2,5-dimethylpiperazin-1-yl)-2-trifluoromethylbenzonitrile synthesized in Reference Example 1-1 was added dropwise to the solution at −78° C., and the mixture was stirred at the same temperature for 1 hour. Next, this was mixed with 400 mg of 40% methylamine methanol solution and stirred at room temperature for 1 hour. The solvent was evaporated, and the residue was dissolved in ethyl acetate, washed with dilute hydrochloric acid, saturated sodium bicarbonate solution and saturated brine in that order and then dried over sodium sulfate. The solvent was evaporated under reduced pressure and the residue was purified by a silica gel column chromatography to obtain 340 mg of the title compound from ethyl acetate-hexane (1:1, v/v) eluate.

Example 15-1 trans-4-(4-Cyano-3-trifluoromethylphenyl)-4'-fluoro-N,2,5-trimethylpiperazine-1-carboxanilide A 69 mg portion of 60% sodium hydride was suspended in 6 ml of DMF, 660 mg of trans-4-(4-cyano-3-trifluoromethylphenyl)-4'-fluoro-2,5-dimethylpiperazine-1-carboxanilide synthesized in Example 1-1 was added to the suspension under ice-cooling, and then the mixture was stirred at 50° C. for 10 minutes. The reaction solution was ice-cooled, 0.11 ml of methyl iodide was added dropwise thereto, and then the mixture was stirred at room temperature for 2 hours. The reaction mixture was mixed with water, extracted with ethyl acetate, washed with saturated brine and then dried over sodium sulfate. The solvent was evaporated under reduced pressure and the residue was purified by a silica gel column chromatography to obtain 620 mg of the title compound from ethyl acetate-hexane eluate.

Compounds of Examples 15-2 and 15-3 were synthesized in the same manner as described in Example 15-1. In this connection, acetic anhydride was used instead of methyl iodide in the case of Example 15-2.

Example 16-1

4-[trans-2,5-Dimethyl-4-(1-oxo-1λ4-thiomorpholine-4-carbonyl)piperazin-1-yl]-2-trifluoromethylbenzonitrile A 270 mg portion of 4-[2,5-dimethyl-4-(thiomorpholine-4-carbonyl)piperazin-1-yl]-2-trifluoromethylbenzonitrile synthesized in Example 7-6 was dissolved in 7 ml of dichloromethane, and the solution was mixed with 110 mg of sodium bicarbonate and 155 mg of m-chloroperbenzoic acid (MCPBA) at −78° C. and stirred at the same temperature for 6 hours. The reaction solution was mixed with chloroform, washed with 1 N aqueous sodium hydroxide and saturated brine and then dried over sodium sulfate. The solvent was evaporated under reduced pressure and the residue was purified by a silica gel column chromatography to obtain 232 mg of the title compound from methanol-chloroform (1:50, v/v) eluate.

Compounds of Examples 16-2 to 16-5 were synthesized in the same manner as described in Example 16-1. In this connection, amount of MCPBA was optionally changed in response to the oxidation state of the product.

Example 17

4-[4-Benzyloxycarbonyl-2-methyl-1-piperazinyl]-2-trifluoromethylbenzonitrile

A 1.01 g portion of benzyl 3-methylpiperazine-1-carboxylate synthesized in Reference Example 10, 814 mg of 4-fluoro-2-trifluoromethylbenzonitrile and 2.38 g of potassium carbonate were added to 20 ml of DMF and stirred at 100° C. for 20 hours. This was mixed with water, extracted with ethyl acetate and dried, and then the solvent was evaporated. The resulting residue was purified by a silica gel column chromatography to obtain 440 mg of the title compound from ethyl acetate-hexane (3:1, v/v) eluate.

Example 18-1

(2R,5S)-trans-4-(4-Cyano-3-trifluoromethylphenyl)-N-(2-chloro-4-pyridyl)-2,5-dimethylpiperazine-1-carboxamide A 3.4 g portion of 2-chloroisonicotinic acid was suspended in 50 ml of acetonitrile, and the suspension was mixed with 2.64 ml of oxalyl chloride and 3 drops of DMF and stirred at room temperature for 40 minutes. This was then mixed with 2.81 g of sodium azide and 9.03 ml of triethylamine and stirred at room temperature for 1 hour. The reaction solution was mixed with water and extracted with ether, and then the solvent was evaporated to obtain crude acid azide. This was dissolved in 30 ml of toluene, and the mixture was heated under reflux for 45 minutes. To the reaction mixture was added 2 g of (2S,5R)-4-(2,5-dimethylpiperazin-1-yl)-2-trifluoromethylbenzonitrile synthesized in Reference Example 11-1 at room temperature, and the reaction mixture was stirred at room temperature for 30 minutes. After evaporation of the solvent, the resulting mixture was subjected to a silica gel column chromatography and eluted with chloroform-methanol (50:1, v/v) to obtain 3.44 g of the title compound. Thereafter, this was crystallized from ethyl acetate-hexane to obtain 2.51 g of crystals of the title compound.

NMR: 1.10 (3H, d, J=6), 1.20 (3H, d, J=6), 3.36–3.51 (2H, m), 3.71–3.78 (1H, m), 3.86–3.93 (1H, m), 4.31–4.43 (1H, m), 4.46–4.56 (1H, m), 7.21–7.35 (2H, m), 7.45–7.55 (1H, m), 7.69 (1H, d, J=2), 7.86 (1H, d, J=9), 8.17 (1H, d, J=6), 9.22 (1H, s)

In the following, synthesis of the compounds of Examples 18-2 to 18-30 was carried out in the same manner as described in Example 18-1 using a racemic or corresponding optically active trans-4-(2,5-dimethylpiperazin-1-yl)-2-trifluoromethylbenzonitrile, trans-2-chloro-4-(2,5-dimethylpiperazin-1-yl)benzonitrile, 4-(piperazin-1-yl)-2-trifluoromethylbenzonitrile or trans-4-(2,5-dimethylpiperazin-1-yl)-2-(2-morpholinoethoxy)benzonitrile. Some of the compounds were isolated as hydrochloride in the usual way.

Example 18-2

(2R,5S)-4-(4-Cyano-3-trifluoromethylphenyl)-2,5-dimethyl-N-(4-pyridyl)piperazine-1-carboxamide monohydrochloride NMR: 1.11 (3H, d, J=7), 1.23 (3H, d, J=7), 3.15–3.90 (3H, m), 3.93–4.29 (1H, m), 4.30–4.50 (1H, m), 4.52–4.85 (1H, m), 7.20–7.40 (2H, m), 7.86 (1H, d, J=9), 8.15 (2H, d, J=7), 8.59 (2H, d, J=7), 10.78 (1H, s), 14.87 (1H, br s)

Example 18-4

(2R,5S)-4-(4-Cyano-3-trifluoromethylphenyl)-2,5-dimethyl-N-(6-trifluoromethyl-3-pyridyl)piperazine-1-carboxamide NMR: 1.12 (3H, d, J=6), 1.22 (3H, d, J=7), 3.35–3.55 (2H, m), 3.72–3.79 (1H, m), 3.87–3.98 (1H, m), 4.32–4.59 (2H, m), 7.24–7.34 (2H, m), 7.80 (1H, d, J=9), 7.86 (1H, d, J=7), 8.15–8.22 (1H, m), 8.86 (1H, d, J=2), 9.17 (1H, s)

Example 18-5

(2R,5S)-4-(4-Cyano-3-trifluoromethylphenyl)-N-(6-fluoro-3-pyridyl)-2,5-dimethylpiperazine-1-carboxamide NMR: 1.11 (3H, d, J=6), 1.20 (3H, d, J=7), 3.39 (1H, dd, J=4, 13), 3.44 (1H, dd, J=3, 14), 3.75 (1H, dd, J=1, 13), 3.89 (1H, br d, J=14), 4.30–4.42 (1H, m), 4.45–4.55 (1H, m), 7.09 (1H, dd, J=2, 9), 7.27 (1H, dd, J=2, 9), 7.31 (1H, d, J=2), 7.85 (1H, d, J=9), 8.05 (1H, ddd, J=3, 8, 9), 8.29 (1H, dd, J=1, 2), 8.83 (1H, s)

Example 18-7

(2R,5S)-N-(6-Cyano-3-pyridyl)-4-(4-cyano-3-trifluoromethylphenyl)-2,5-dimethylpiperazine-1-carboxamide NMR: 1.11 (3H, d, J=7), 1.22 (3H, d, J=6), 3.36–3.54 (2H, m), 3.68–3.82 (1H, m), 3.84–3.98 (1H, m), 4.31–4.45 (1H, m), 4.46–4.60 (1H, m), 7.20–7.36 (2H, m), 7.86 (1H, d, J=9), 7.91 (1H, d, J=9), 8.15 (1H, dd, J=2, 9), 8.85 (1H, d, J=2), 9.26 (1H, s)

Example 18-8

(2R,5S)-4-(4-Cyano-3-trifluoromethylphenyl)-N-(2-fluoro-4-pyridyl)-2,5-dimethylpiperazine-1-carboxamide NMR: 1.09 (3H, d, J=7), 1.20 (3H, d, J=7), 3.35–3.52 (2H, m), 3.68–3.82 (1H, m), 3.89 (1H, d, J=13), 4.30–4.44 (1H, m), 4.45–4.57 (1H, m), 7.22–7.35 (3H, m), 7.40 (1H, d, J=6), 7.86 (1H, d, J=9), 8.00 (1H, d, J=6), 9.29 (1H, s)

Example 18-9

(2R,5S)-4-(4-Cyano-3-trifluoromethylphenyl)-2,5-dimethyl-N-(2-trifluoromethyl-4-pyridyl)piperazine-1-carboxamide NMR: 1.10 (3H, d, J=6), 1.21 (3H, d, J=6), 3.40 (1H, dd, J=6, 14), 3.47 (1H, br d, J=12), 3.76 (1H, br d, J=12), 3.91

(1H, d, J=14), 4.34–4.43 (1H, m), 4.48–4.56 (1H, m), 7.29 (1H, dd, J=2, 9), 7.31 (1H, d, J=2), 7.79 (1H, dd, J=2, 6), 7.86 (1H, d, J=9), 8.06 (1H, d, J=2), 8.51 (1H, d, J=6), 9.37 (1H, s)

Example 19-1

(2R,5S)-4-(4-Cyano-3-trifluoromethylphenyl)-N-(2-methoxy-6-methyl-4-pyridyl)-2,5-dimethylpiperazine-1-carboxamide A 6.1 ml portion of 1 N aqueous sodium hydroxide was added to 10 ml of THF containing 1.20 g of 2-methoxy-6-methyl-4-pyridinecarboxylic acid ethyl ester and stirred at room temperature for 1 hour and 20 minutes, and then the reaction solvent was evaporated to obtain 2-methoxy-6-methyl-4-pyridinecarboxylic acid sodium salt. Thereafter, the title compound was obtained by the same procedure of Example 18-1.

NMR: 1.08 (3H, d, J=6), 1.17 (3H, d, J=6), 2.30 (3H, s), 3.35–3.45 (2H, m), 3.69–3.75 (1H, m), 3.78 (3H, s), 3.83–3.89 (1H, m), 4.32–4.40 (1H, m), 4.45–4.54 (1H, m), 6.82–6.85 (1H, m), 6.97–6.99 (1H, m), 7.23–7.31 (2H, m), 7.84 (1H, d, J=9), 8.83 (1H, s)

Compounds of Examples 19-2 to 19-6 were synthesized in the same manner.

Example 19-2

(2R,5S)-4-(4-Cyano-3-trifluoromethylphenyl)-N-(2-ethyl-6-methoxy-4-pyridyl)-2,5-dimethylpiperazine-1-carboxamide NMR: 0.80–0.93 (4H, m), 1.84–1.95 (1H, m), 3.73 (3H, s), 6.78 (1H, d, J=2), 7.03 (1H, d, J=2), 7.21–7.33 (2H, m), 7.85 (1H, d, J=9), 8.82 (1H, s)

Example 20

(2R,5S)-N-(2-Acetyl-4-pyridyl)-4-(4-cyano-3-trifluoromethylphenyl)-2,5-dimethylpiperazine-1-carboxamide While stirring with ice-cooling, 12.5 ml of trifluoroacetic acid was added to 12.5 ml of chloroform solution containing 1.41 g of 2-acetyl-4-pyridinylcarbamic acid t-butyl ester. The mixture was immediately warmed up to room temperature and stirred for 2 hours and 40 minutes. The solvent was evaporated under reduced pressure to obtain a crude amine. This compound was dissolved in 25 ml of pyridine, and the solution was mixed with 0.83 ml of phenyl chloroformate while stirring with ice-cooling and then immediately warmed up to room temperature. After 8 hours and 30 minutes, this was mixed with 10 ml of pyridine solution containing 1.4 g of (2S,5R)-4-(2,5-dimethylpiperazin-1-yl)-2-trifluoromethylbenzonitrile and heated under reflux for 1 hour. The reaction mixture cooled to room temperature was mixed with water and extracted with chloroform. The organic layer was washed with saturated brine and dried over anhydrous sodium sulfate, and then the solvent was evaporated under reduced pressure. The residue was purified by a silica gel column chromatography to obtain 1.03 g of the title compound from methanol-chloroform (1:99, v/v) eluate.

NMR: 1.10 (3H, d, J=7), 1.20 (3H, d, J=7), 2.61 (3H, s), 3.34–3.52 (2H, m), 3.75 (1H, d, J=14), 3.92 (1H, d, J=14), 4.28–4.45 (1H, m), 4.46–4.62 (I H, m), 7.20–7.35 (2H, m), 7.78–7.91 (2H, m), 8.12 (1H, d, J=2), 8.48 (1H, d, J=6), 9.24(1H, s)

Example 21

(2R,5S)-N-(2-Amino-pyrimidin-4-yl)-4-(4-cyano-3-trifluoromethylphenyl)-2,5-dimethylpiperazine-1-carboxamide A 15 ml portion of trifluoroacetic acid was added to 60 ml of dichloroethane solution containing 2.8 g of (2R,5S)-4-(4-cyano-3-trifluoromethylphenyl)-N-[2-(1,1-dimethylethoxycarbonyl)amino-4-pyrimidyl]-2,5-dimethylpiperazine-1-carboxamide synthesized in Example 6-2, and the mixture was stirred at room temperature for about 12 hours. The reaction solution was evaporated under reduced pressure, and the thus obtained residue was mixed with saturated sodium bicarbonate solution and extracted with chloroform. The thus obtained organic layer was washed with water and dried over anhydrous magnesium sulfate, and then the crude product obtained by evaporating the solvent was subjected to a silica gel column chromatography to obtain 1.97 g of the title compound from chloroform-methanol (30:1, v/v) eluate. Thereafter, this was crystallized from ethyl acetate-hexane to obtain 1.51 g of the title compound as crystals.

NMR: 1.08 (3H, d, J=7), 1.16(3H, d, J=7), 3.36–3.43 (2H, m), 3.70 (1H, dd, J 2, 13), 3.88 (1H, d, J=13), 4.33(1H, br s), 4.50(1H, br s), 6.19 (2H, s), 6.99 (1H, d, J=6), 7.23(1H, dd, J=2, 9), 7.29(1H, d, J=2), 7.83 (1H, d, J=9), 8.01 (1H, d, J=6), 9.17 (1H, s)

Example 22-1

(+/−)-trans-N-(2-Acetylamino-pyrimidin-4-yl)-4-(4-cyano-3-trifluoromethylphenyl)-2,5-dimethylpiperazine-1-carboxamide A 1.2 ml portion of acetic anhydride was added to 10 ml of pyridine solution containing 0.51 g of (+/−)-trans-N-(2-amino-pyrimidin-4-yl)-4-(4-cyano-3-trifluoromethylphenyl)-2,5-dimethylpiperazine-1-carboxamide synthesized in the same manner as described in Example 21, and the mixture was stirred at room temperature for about 12 hours and then heated at 70° C. for about 1 hour. The reaction solution was evaporated under reduced pressure, and the thus obtained residue was mixed with 0.5 N aqueous sodium hydroxide and extracted with chloroform. The thus obtained organic layer was washed with water and dried over anhydrous magnesium sulfate, and then the crude product obtained by evaporating the solvent was separated by a silica gel column chromatography to obtain 0.46 g of the title compound from chloroform-methanol-28% aqueous ammonia (500:9:1, v/v/v) eluate. Thereafter, this was crystallized from ethyl acetate-hexane solution to obtain 0.31 g of white crystals.

Compound of Example 22-2 was synthesized in the same manner.

Example 23-1

(+/−)-trans-N-(2-Amino-pyridin-4-yl)-4-(4-cyano-3-trifluoromethylphenyl)-2,5-dimethylpiperazine-1-carboxamide A 50 ml portion of t-butanol solution containing 1.38 g of (+/−)-trans-4-{[4-(4-cyano-3-trifluoromethylphenyl)-2,5-dimethylpiperazine-1-carbonyl]amino}pyridine-2-carboxylic acid synthesized in the same manner as described in Example 12-1, 1.5 ml of DPPA and 1.5 ml of triethylamine was heated under reflux for 8 hours, and then the solvent was evaporated under reduced pressure. This was mixed with 30 ml of trifluoroacetic acid and stirred at room temperature for 1 hour, the solvent was evaporated under reduced pressure, and then the resulting residue was alkalified with saturated sodium bicarbonate solution. Next, this was extracted with ethyl acetate, the organic layer was washed with purified water and then with saturated brine and dried over anhydrous sodium sulfate, and then the solvent was evaporated under reduced pressure. The residue was purified by a silica gel column chromatography to obtain 0.94 g of the title compound from chloroform-methanol (10:1, v/v) eluate. Thereafter, this was crystallized from ethyl acetate-hexane to obtain 0.72 g of the title compound as white crystals.

Compound of Example 23-2 was synthesized in the same manner.

Example 24 trans-N-(6-Aminosulfonyl-3-pyridyl)-4-(4-cyano-3-trifluoromethylphenyl)-2,5-dimethylpiperazine-1-carboxamide A 7.3 ml portion of 1.54 M pentane solution of tert-butyl lithium was added dropwise to 100 ml of THF solution containing 2.48 g of trans-4-(4-cyano-3-trifluoromethylphenyl)-N-(6-methanesulfonyl-3-pyridyl)-2,5-dimethylpiperazine-1-carboxamide at −78° C., and then the mixture was stirred at −30° C. for 15 minutes. After cooling again to −78° C., this was mixed with 15.5 ml of 1.0 M tetrahydrofuran solution of tri-n-butyl borane, warmed up to room temperature spending 1 hour and then heated under refulx for 18 hours. Under ice-cooling, this was mixed with 5.91 g of sodium acetate, 50 ml of water and 491 mg of hydroxylamine-O-sulfonic acid and stirred overnight at room temperature. The reaction mixture was extracted with ethyl acetate, the organic layer was washed with saturated sodium bicarbonate solution and saturated brine in that order and dried over magnesium sulfate, and then the solvent was evaporated. The thus obtained mixture was subjected to a silica gel column chromatography and eluted with chloroform-methanol (9:1, v/v) to obtain 414 mg of the title compound. Thereafter, this was crystallized twice from ethanol to obtain 271 mg of the title compound as crystals.

In addition to the above examples, compounds of Examples 25 to 28 can also be synthesized by the methods disclosed in the specification or by employing general synthesis methods.

Structures and physical data of the compounds of the above examples are shown in the following tables.

In this connection, symbols in the tables are as defined in the tables of Reference Examples, and other symbols have the following meanings.

Ex.: Example No.
DATA: Physical data
mp: Melting point ° C. (recrystallization solvent)
Ms: Mass spectrometry values
i-Pr: Isopropyl
t-Bu: t-Butyl
Ac: Acetyl
c-Pr: Cyclopropyl
py: pyridyl
Pm: Pyrimidinyl
Im: Imidazolyl
Qy: Quinolyl
Mor: Morpholinyl
AcOEt: Ethyl acetate
EtOH: Ethanol
(Et)2O: Diethyl ether
1,2-diCl-Et: 1,2-Dichloroethane
(i-Pr)2O: Diisopropyl ether
MeOH: Methanol
i-PrOH: Isopropanol
Hex: Hexane

TABLE 7

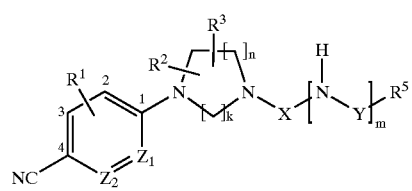

| Ex. | $R^1$ | $Z_1$ | $Z_2$ | $R^2$ | $R^3$ | k | n | X | Y | m | $R^5$ | Substituent on $R^5$ | DATA | Remarks |
|---|---|---|---|---|---|---|---|---|---|---|---|---|---|---|
| 1-1 | 3-CF3 | CH | CH | 2-Me | 5-Me | 2 | 1 | CO | — | 1 | Ph | 4-F | mp: 200–203 (acetone-i-Pr2O) | trans |
| 1-2 | 3-CF3 | CH | CH | H | H | 3 | 1 | CO | — | 1 | Ph | 4-F | mp: 179–180 (AcOEt) | |
| 1-3 | 3-CF3 | CH | CH | 2-Me | 5-Me | 2 | 1 | CO | — | 1 | Ph | 4-OCF3 | MS (FAB) m/z 487 [(M+H)+] | trans |
| 1-4 | 3-CF3 | CH | CH | 2-Me | 5-Me | 2 | 1 | CO | — | 1 | Ph | 4-NO2 | MS (FAB) m/z 446 [(M−H)−] | trans |
| 1-5 | 3-CF3 | CH | CH | 2-Me | 5-Me | 2 | 1 | CO | — | 1 | Ph | 4-OMe | MS (FAB) m/z 433 [(M+H)+] | trans |
| 1-6 | 3-CF3 | CH | CH | 2-Me | 5-Me | 2 | 1 | CO | — | 1 | Ph | 4-CN | MS (FAB) m/z 428 [(M+H)+] | trans |
| 1-7 | 3-CF3 | CH | CH | 2-Me | 5-Me | 2 | 1 | CO | — | 1 | Ph | 4-COOEt | MS (FAB) m/z 475 [(M+H)+] | trans |
| 1-8 | 3-CF3 | CH | CH | 2-Me | 5-Me | 2 | 1 | CO | — | 1 | Ph | 4-Ac | MS (FAB) m/z 445 [(M+H)+] | trans |
| 1-9 | 3-CF3 | CH | CH | 2-Me | 5-Me | 2 | 1 | CO | — | 1 | Ph | 2,4,6-triF | MS (FAB) m/z 457 [(M+H)+] | trans |
| 1-10 | 3-CF3 | CH | CH | 2-Me | 5-Me | 2 | 1 | CO | — | 1 | Ph | 4-SMe | MS (FAB) m/z 449 [(M+H)+] | trans |
| 1-11 | 3-CF3 | CH | CH | 2-Me | 6-Me | 2 | 1 | CO | — | 1 | Ph | 4-F | mp: 205 (AcOEt) | cis |
| 1-12 | H | CH | CH | 2-Me | 5-Me | 2 | 1 | CO | — | 1 | Ph | 4-F | MS (FAB) m/z 353 [(M+H)+] | trans |
| 1-13 | 2-F | CH | CH | 2-Me | 5-Me | 2 | 1 | CO | — | 1 | Ph | 4-F | MS (FAB) m/z 371 [(M+H)+] | trans |
| 1-14 | 3-CN | CH | CH | 2-Me | 5-Me | 2 | 1 | CO | — | 1 | Ph | 4-CN | MS (FAB) m/z 385 [(M+H)+] | trans |
| 1-15 | 2-CF3 | CH | CH | 2-Me | 5-Me | 2 | 1 | CO | — | 1 | Ph | 4-F | MS (FAB) m/z 421 [(M+H)+] | trans |
| 1-16 | 3-CF3 | CH | CH | 3-Me | H | 2 | 1 | CO | — | 1 | Ph | 4-F | mp: 197–199 (AcOEt-i-Pr2O) | |
| 1-17 | 3-CF3 | CH | CH | 3-Et | H | 2 | 1 | CO | — | 1 | Ph | 4-F | mp: 180–182 (AcOEt-i-Pr2O) | |

TABLE 7-continued

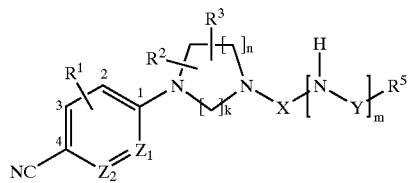

| Ex. | R¹ | Z₁ | Z₂ | R² | R³ | k | n | X | Y | m | R⁵ | Substituent on R⁵ | DATA | Remarks |
|---|---|---|---|---|---|---|---|---|---|---|---|---|---|---|
| 1-18 | 3-CF3 | CH | CH | 3-iPr | H | 2 | 1 | CO | — | 1 | Ph | 4-F | MS (FAB) m/z 435 [(M+H)+] | trans |
| 1-19 | 3-CF3 | CH | CH | 2-Me | H | 2 | 1 | CO | — | 1 | Ph | 2,4-diF | MS (FAB) m/z 425 [(M+H)+] | trans |
| 1-20 | 3-CF3 | CH | CH | 2-Me | 5-Me | 2 | 1 | CO | — | 1 | Cyclohexyl | — | MS (FAB) m/z 409 [(M+H)+] | trans |
| 1-21 | 3-Cl | CH | CH | 2-Me | 5-Me | 2 | 1 | CO | — | 1 | t-Bu | — | MS (FAB) m/z 349 [(M+H)+] | trans |
| 1-22 | 3-CF3 | CH | CH | 2-Me | 5-Me | 2 | 1 | CO | — | 1 | Et | — | MS (FAB) m/z 355 [(M+H)+] | trans |
| 1-23 | H | N | CH | 2-Me | 5-Me | 2 | 1 | CO | — | 1 | Ph | 4-F | MS (FAB) m/z 354 [(M+H)+] | trans |
| 1-24 | 3-F | CH | CH | 2-Me | 5-Me | 2 | 1 | CO | — | 1 | Ph | 4-F | mp: 175–176 (AcOEt—Hex) | trans |
| 1-25 | 3-Br | CH | CH | 2-Me | 5-Me | 2 | 1 | CO | — | 1 | Ph | 2,4-diF | mp: 179–180 (AcOEt—Hex) | trans |
| 1-26 | 3-OMe | CH | CH | 2-Me | 5-Me | 2 | 1 | CO | — | 1 | Ph | 2,4-diF | mp: 174–176 (AcOEt—Hex) | trans |
| 1-27 | 3-Me | CH | CH | 2-Me | 5-Me | 2 | 1 | CO | — | 1 | Ph | 2,4-diF | mp: 197–198 (AcOEt) | trans |
| 1-28 | 3-CF3 | CH | CH | 2-Me | 5-Me | 2 | 1 | SO2 | — | 0 | Ph | 4-F | MS (FAB) m/z 442 [(M+H)+] | trans |
| 1-29 | 3-CF3 | CH | CH | 3-Me | 5-Me | 2 | 1 | CO | — | 0 | Ph | 4-F | mp: 181–182 (i-Pr2O) | cis |
| 1-30 | 3-CF3 | CH | CH | 2-Me | 5-Me | 2 | 1 | CO | — | 1 | Ph | 4-F | MS (FAB) m/z 437 [(M+H)+] | trans |
| 1-31 | 3-CF3 | CH | CH | 2-Me | 5-Me | 2 | 1 | CO | CO | 1 | Ph | 4-F | MS (FAB) m/z 449 [(M+H)+] | trans |
| 1-32 | 3-CF3 | CH | CH | 2-Me | 5-Me | 2 | 1 | CO | — | 0 | —O—CH2—Ph | — | MS (FAB) m/z 418 [(M+H)+] | trans |
| 1-34 | 3-CF3 | CH | CH | H | H | 2 | 1 | CO | — | 1 | Ph | 4-F | mp: 214–217 (CH2Cl2) | |
| 1-35 | 3-CF3 | CH | CH | 2-Me | 5-Me | 2 | 1 | CO | — | 1 | Ph | — | MS (FAB) m/z 403 [(M+H)+] | trans |
| 1-36 | 3-CF3 | CH | CH | 2-Me | 5-Me | 2 | 1 | CO | — | 1 | Ph | 4-CF3 | MS (FAB) m/z 471 [(M+H)+] | trans |
| 1-37 | 3-CF3 | CH | CH | 2-Me | 5-Me | 2 | 1 | CO | — | 1 | Ph | 4-Cl | MS (FAB) m/z 437 [(M+H)+] | trans |
| 1-38 | 3-CF3 | CH | CH | 2-Me | 5-Me | 2 | 1 | CO | — | 1 | Ph | 3-F | MS (FAB) m/z 421 [(M+H)+] | trans |
| 1-39 | 3-CF3 | CH | CH | 2-Me | 5-Me | 2 | 1 | CO | — | 1 | Ph | 2-F | MS (FAB) m/z 421 [(M+H)+] | trans |
| 1-40 | 3-CF3 | CH | CH | 2-Me | 5-Me | 2 | 1 | CO | CH2 | 1 | Ph | — | MS (FAB) m/z 417 [(M+H)+] | trans |
| 1-41 | 3-CF3 | CH | CH | 2-Me | 5-Me | 2 | 1 | CO | — | 1 | Ph | 4-OPh | MS (FAB) m/z 495 [(M+H)+] | trans |
| 1-42 | 3-CF3 | CH | CH | 2-Me | 5-Me | 2 | 1 | CO | — | 1 | Ph | 4-i-Pr | MS (FAB) m/z 445 [(M+H)+] | trans |
| 1-43 | 3-CF3 | CH | CH | 2-Me | 5-Me | 2 | 1 | CO | — | 1 | Ph | 3,4-diF | MS (FAB) m/z 439 [(M+H)+] | trans |
| 1-44 | 3-CF3 | CH | CH | 2-Me | 5-Me | 2 | 1 | CO | — | 1 | Ph | 2,4-diF | MS (FAB) m/z 439 [(M+H)+] | trans |
| 1-45 | 3-CF3 | CH | CH | 2-Me | 5-Me | 2 | 1 | CC | — | 1 | Ph | 4-Br | MS (FAB) m/z 481 [(M+H)+] | trans |
| 1-46 | 3-CF3 | CH | CH | 2-Me | 5-Me | 2 | 1 | CO | — | 1 | Ph | 3-CN | MS (FAB) m/z 428 [(M+H)+] | trans |
| 1-47 | 3-CF3 | CH | CH | 2-Me | 5-Me | 2 | 1 | CO | — | 1 | Ph | 3,5-diF | MS (FAB) m/z 439 [(M+H)+] | trans |
| 1-48 | 3-CF3 | CH | CH | 2-Me | 5-Me | 2 | 1 | CO | — | 1 | Ph | 2-OMe | MS (FAB) m/z 433 [(M+H)+] | trans |
| 1-49 | 3-CF3 | CH | CH | 2-Me | 5-Me | 2 | 1 | CO | — | 1 | Ph | 3-OMe | MS (FAB) m/z 433 [(M+H)+] | trans |
| 1-50 | 3-Cl | CH | CH | 2-Me | 5-Me | 2 | 1 | CO | — | 1 | Ph | 4-F | MS (FAB) m/z 387 [(M+H)+] | trans |
| 1-51 | 3-CN | CH | CH | 2-Me | 5-Me | 2 | 1 | CO | — | 1 | Ph | 4-F | MS (FAB) m/z 378 [(M+H)+] | trans |
| 1-52 | 3-CF3 | CH | CH | 2-Me | 5-Me | 2 | 1 | CO | — | 1 | Ph | 4-F | mp: 257–260 (i-Pr2O) | trans |
| 1-53 | 3-CF3 | CH | CH | 3-Me | 3-Me | 2 | 1 | CO | — | 1 | Ph | 4-F | mp: 179–180 (AcOEt-i-Pr2O) | |
| 1-54 | 3-CF3 | CH | CH | 2-Me | H | 2 | 1 | CO | — | 1 | Ph | 2,4-diF | mp: 144–145 (AcOEt-i-Pr2O) | |
| 1-55 | 3-CF3 | CH | CH | 2-Me | H | 2 | 1 | CO | — | 1 | Ph | 2-CF3, 4-F | mp: 146–148 (AcOEt—Hex) | |
| 1-56 | 3-Cl | CH | CH | 2-Me | 5-Me | 2 | 1 | CO | — | 1 | Ph | 2-Br, 4-F | MS (FAB) m/z 465 [(M+H)+] | trans |

TABLE 7-2

| Ex. | Structure | DATA | Remarks |
|---|---|---|---|
| 1-33 | (4-nitro-2-trifluoromethylphenyl piperazine with 2,5-dimethyl substituents, N-(4-fluorophenyl)urea) | mp: 182(AcOEt) | trans |

TABLE 8

| Ex. | R² | R³ | k | n | X | Y | m | R⁵ | Substituent on R⁵ | DATA | Remarks |
|---|---|---|---|---|---|---|---|---|---|---|---|
| 2-1 | 2-Me | 5-Me | 2 | 1 | CO | — | 1 | 2-Thienyl | — | MS (FAB) m/z 409 [(M+H)+] | trans |
| 2-2 | 2-Me | 5-Me | 2 | 1 | CO | — | 1 | 2-Furyl | — | MS (FAB) m/z 407 [(M+H)+] | trans |
| 2-3 | 2-Me | 5-Me | 2 | 1 | CO | — | 1 | 3-Py | — | mp: 183 (AcOEt) | trans |
| 2-4 | 2-Me | 5-Me | 2 | 1 | CO | — | 1 | 3-Py | 2-F | MS (FAB) m/z 422 [(M+H)+] | trans |
| 2-5 | 2-Me | 5-Me | 2 | 1 | CO | — | 1 | 4-Py | — | MS (FAB) m/z 404 [(M+H)+] | trans |
| 2-6 | 2-Me | 5-Me | 2 | 1 | CO | — | 1 | 3-Py | 6-Me | mp: 233–234 (AcOEt) | trans |
| 2-7 | 2-Me | 5-Me | 2 | 1 | CO | — | 1 | 3-Py | 2-OMe | mp: 174–176 (AcOEt) | trans |
| 2-8 | 2-Me | 5-Me | 2 | 1 | CO | — | 1 | Ph | 2-CN | MS (FAB) m/z 428 [(M+H)+] | trans |
| 2-9 | 2-Me | 5-Me | 2 | 1 | CO | — | 1 | 3-Py | 5-CN | MS (FAB) m/z 429 [(M+H)+] | trans |
| 3-1 | 2-Me | 5-Me | 2 | 1 | CO | (CH2)2 | 1 | Ph | — | MS (FAB) m/z 431 [(M+H)+] | trans |
| 3-2 | 2-Me | 5-Me | 2 | 1 | CO | CH2 | 1 | 1-Naphtyl | — | MS (FAB) m/z 467 [(M+H)+] | trans |
| 3-3 | 2-Me | 5-Me | 2 | 1 | CO | — | 1 | Pyrazine-2-yl | — | mp: 167 (AcOEt—Hex) | trans |
| 3-4 | 2-Me | 5-Me | 2 | 1 | CO | CH2 | 1 | Ph | 4-F | MS (FAB) m/z 435 [(M+H)+] | trans |
| 4 | 2-Me | 5-Me | 2 | 1 | CO | — | 1 | Ph | 2,4-diBr | MS (FAB) m/z 509, 511 [M+H]+ | trans |
| 5-1 | 2-Me | 5-Me | 2 | 1 | CO | —C(CH3)2— | 1 | Ph | — | mp: 152.5–153.5 (AcOEt—Hex) | trans |
| 5-2 | 3-Me | 3-Me | 2 | 1 | CO | — | 1 | 3-Py | — | MS (FAB) m/z 404 [(M+H)+] | |
| 5-3 | 3-Me | 3-Me | 2 | 1 | CO | — | 1 | Pyrazine-2-yl | — | mp: 173–174 (AcOEt—Hex) | |
| 6-1 | 2-Me | 5-Me | 2 | 1 | CO | — | 1 | 4-Py | 2-Br | MS (FAB) m/z 482 [(M+H)+] | (2R, 5S) |
| 6-2 | 2-Me | 5-Me | 2 | 1 | CO | — | 1 | 4-Pm | 2-tBuOCONH— | MS (FAB) m/z 518 [(M+H)+] | (2R, 5S) |
| 6-3 | 2-Me | 5-Me | 2 | 1 | CO | — | 1 | 4-Py | 2-Im-1-yl | mp: 238–240 (AcOEt—Hex) | trans |
| 6-4 | 2-Me | 5-Me | 2 | 1 | CO | — | 1 | 4-Py | 3-COPh | MS (FAB) m/z 508 [(M+H)+] | trans |
| 6-5 | 2-Me | 5-Me | 2 | 1 | CO | — | 1 | Isoxazol-3-yl | 5-Me | MS (FAB) m/z 408 [(M+H)+] | trans |
| 6-6 | 2-Me | 5-Me | 2 | 1 | CO | — | 1 | Ph | 4-Im-1-yl | mp: >210 (EtOH) | trans monohydrochloride |
| 6-7 | 2-Me | 5-Me | 2 | 1 | CO | — | 1 | 1,3,4-Thiazazol-2-yl | — | MS (FAB) m/z 411 [(M+H)+] | trans |
| 6-8 | 2-Me | 5-Me | 2 | 1 | CO | — | 1 | Thiazol-2-yl | — | mp: 180–182 (AcOEt—Hex) | trans |
| 6-9 | 2-Me | 5-Me | 2 | 1 | CO | — | 1 | Im-2-yl | 1-Me | mp: 190–192 (AcOEt—Hex) | trans |
| 6-10 | 2-Me | 5-Me | 2 | 1 | CO | — | 1 | Benzothiazol-6-yl | — | MS (FAB) m/z 460 [(M+H)+] | trans |
| 6-11 | 2-Me | 5-Me | 2 | 1 | CO | — | 1 | Benzoimidazol-2-yl | — | MS (FAB) m/z 443 [(M+H)+] | trans |
| 6-12 | 2-Me | 5-Me | 2 | 1 | CO | — | 1 | 2-Py | — | mp: 195–197 (AcOEt-EtOH) | trans |
| 6-13 | 2-Me | 5-Me | 2 | 1 | CO | — | 1 | 3-Py | 6-OMe | mp: 184–185 (AcOEt—Hex) | (2R, 5S) |
| 6-14 | 2-Me | 5-Me | 2 | 1 | CO | — | 1 | Tetrazol-5-yl | — | MS (FAB) m/z 417 [(M+H)+] | trans |
| 6-15 | 2-Me | 5-Me | 2 | 1 | CO | — | 1 | 3-Py | 2-NO2 | MS (FAB) m/z 447 [(M−H)−] | trans |
| 6-16 | 2-Me | 5-Me | 2 | 1 | CO | — | 1 | 2-Py | 3-Me | mp: 119.5–121.0 | trans monohydrochloride |

TABLE 9

| Ex | R² | R³ | k | n | X | R⁴ | Y | m | R⁵ | Substituent on R⁵ | DATA | Remarks |
|---|---|---|---|---|---|---|---|---|---|---|---|---|
| 7-1 | 2-Me | 5-Me | 2 | 1 | CO | H | CH2 | 1 | 3-Py | 6-OMe | MS (FAB) m/z 448 [(M+H)+] | (2R, 5S) |
| 7-2 | 2-Me | 5-Me | 2 | 1 | CO | H | (CH2)2 | 1 | Mor | — | MS (FAB) m/z 440 [(M+H)+] | trans |
| 7-3 | 2-Me | 5-Me | 2 | 1 | CO | H | CH2 | 1 | Tetrahydrofuran-2-yl | — | mp: 142–143.5 (AcOEt—Hex) | trans |
| 7-4 | 2-Me | 5-Me | 2 | 1 | CO | H | CH2 | 1 | COOEt | — | MS (FAB) m/z 413 [(M+H)+] | trans |
| 7-5 | 2-Me | 5-Me | 2 | 1 | CO | H | (CH2)2 | 1 | 4-Py | — | MS (FAB) m/z 432 [(M+H)+] | trans |
| 7-6 | 2-Me | 5-Me | 2 | 1 | CO | | | | R4 + R5: Thiomorpholino-4-yl | | MS (FAB) m/z 413 [(M+H)+] | trans |
| 7-7 | 2-Me | 5-Me | 2 | 1 | CO | H | CH2 | 1 | 3-Py | 6-Cl | MS (FAB) m/z 452 [(M+H)+] | trans |
| 7-8 | 2-Me | 5-Me | 2 | 1 | CO | H | CH2 | 1 | 2-Py | 6-Cl | mp: 157–159 (AcOEt—Hex) | trans |
| 7-9 | 2-Me | 5-Me | 2 | 1 | CO | H | CH2 | 1 | 3-Py | — | mp: 138–139 (AcOEt—Hex) | trans |
| 7-10 | 2-Me | 5-Me | 2 | 1 | CO | H | CH2 | 1 | Pyrazine-2-yl | — | mp: 118.5–120.5 (AcOEt—Hex) | trans |
| 7-11 | 2-Me | 5-Me | 2 | 1 | CO | H | CH2 | 1 | 2-Py | 3-Me | MS (FAB) m/z 432 [(M+H)+] | trans |
| 8-1 | 2-Me | 2-Me | 1 | 1 | CO | H | — | 1 | Ph | 4-F | mp: 199–200 (i-Pr2O) | trans |
| 8-2 | H | H | 1 | 3 | CO | H | — | 1 | Ph | 4-F | mp: 163–164 (i-Pr2O) | |
| 9 | 2-Me | 5-Me | 2 | 1 | SO2 | H | — | 1 | Ph | 4-NH2 | MS (FAB) m/z 457 [(M+H)+] | trans |
| 10 | 2-Me | 5-Me | 2 | 1 | CO | H | — | 1 | Ph | 4-NH2 | MS (FAB) m/z 418 [(M+H)+] | trans |

TABLE 9-continued

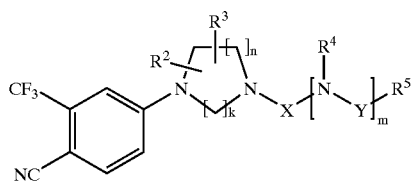

| Ex | R² | R³ | k | n | X | R⁴ | Y | m | R⁵ | Substituent on R⁵ | DATA | Remarks |
|---|---|---|---|---|---|---|---|---|---|---|---|---|
| 11 | 2-Me | 5-Me | 2 | 1 | CO | H | — | 1 | Ph | 4-NHCOMe | MS (FAB) m/z 460 [(M+H)+] | trans |
| 12-1 | 2-Me | 5-Me | 2 | 1 | CO | H | — | 1 | 4-Py | 2-COOH | MS (FAB) m/z 446 [(M–H)–] | (2R, 5S) |
| 12-2 | 2-Me | 5-Me | 2 | 1 | CO | H | — | 1 | Ph | 4-COOH | MS (FAB) m/z 447 [(M+H)+] | trans |
| 12-3 | 2-Me | 5-Me | 2 | 1 | CO | H | — | 1 | 3-Py | 6-COOH | MS (FAB) m/z 448 [(M+H)+] | (2R, 5S) |
| 13-1 | 2-Me | 5-Me | 2 | 1 | CO | H | — | 1 | 4-Py | 2-CONHMe | MS (FAB) m/z 461 [(M+H)+] | (2R, 5S) |
| 13-2 | 2-Me | 5-Me | 2 | 1 | CO | H | — | 1 | Ph | 4-CONHMe | MS (FAB) m/z 460 [(M+H)+] | trans |
| 13-3 | 2-Me | 5-Me | 2 | 1 | CO | H | — | 1 | Ph | 4-CONMe2 | MS (FAB) m/z 474 [(M+H)+] | trans |
| 13-4 | 2-Me | 5-Me | 2 | 1 | CO | H | — | 1 | Ph | 4-CONH2 | MS (FAB) m/z 446 [(M+H)+] | trans |
| 14 | 2-Me | 5-Me | 2 | 1 | CO | H | — | 1 | Ph | 4-SO2NHMe | MS (FAB) m/z 496 [(M+H)+] | trans |
| 15-1 | 2-Me | 5-Me | 2 | 1 | CO | Me | — | 1 | Ph | 4-F | MS (FAB) m/z 435 [(M+H)+] | trans |
| 15-2 | 2-Me | 5-Me | 2 | 1 | CO | COMe | — | 1 | Ph | 2,4-diF | MS (FAB) m/z 481 [(M+H)+] | trans |
| 15-3 | 2-Me | 5-Me | 2 | 1 | CO | Me | CH2 | 1 | 2-Py | — | MS (FAB) m/z 432 [(M+H)+] | trans |
| 16-1 | 2-Me | 5-Me | 2 | 1 | CO | R4 + R5: 1-oxo-thiomorpholino-4-yl | | | | | mp: 173–175 (AcOEt—Hex) | trans |
| 16-2 | 2-Me | 5-Me | 2 | 1 | CO | H | — | 1 | Ph | 4-SO2Me | MS (FAB) m/z 481 [(M+H)+] | trans |
| 16-3 | 2-Me | 5-Me | 2 | 1 | CO | H | — | 1 | 4-Py | 2-SOMe | MS (FAB) m/z 466 [(M+H)+] | trans |
| 16-4 | 2-Me | 5-Me | 2 | 1 | CO | H | — | 1 | 3-Py | 6-SOMe | MS (FAB) m/z 482 [(M+H)+] | trans |
| 16-5 | 2-Me | 5-Me | 2 | 1 | CO | R4 + R5: 1,1-dioxo-thiomorpholino-4-yl | | | | | mp: 243–245 (AcOEt) | trans |
| 17 | 2-Me | 5-H | 2 | 1 | CO | — | — | 0 | O—CH2—Ph | — | MS (FAB) m/z 404 [(M+H)+] | trans |

TABLE 10

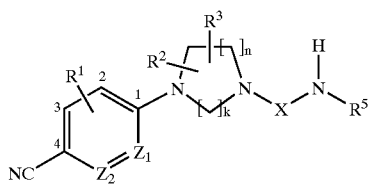

| Ex | R¹ | Z₁ | Z₂ | R² | R³ | k | n | X | R⁵ | Substituent on R⁵ | DATA | Remarks |
|---|---|---|---|---|---|---|---|---|---|---|---|---|
| 18-1 | 3-CF3 | CH | CH | 2-Me | 5-Me | 2 | 1 | CO | 4-Py | 2-Cl | mp: 212–214(AcOEt—Hex) | (2R, 5S) |
| 18-2 | 3-CF3 | CH | CH | 2-Me | 5-Me | 2 | 1 | CO | 4-Py | — | mp: >200(EtOH-iPr2O) | (2R, 5S) mono-hydrochloride |
| 18-3 | 3-CF3 | CH | CH | 2-Me | 5-Me | 2 | 1 | CO | 4-Py | 2-COOMe | MS (FAB) m/z 462 [(M+H)+] | (2R, 5S) |
| 18-4 | 3-CF3 | CH | CH | 2-Me | 5-Me | 2 | 1 | CO | 3-Py | 6-CF3 | mp: 181–183(AcOEt—Et2O) | (2R, 5S) |
| 18-5 | 3-CF3 | CH | CH | 2-Me | 5-Me | 2 | 1 | CO | 3-Py | 6-F | mp: 163–165(AcOEt—Hex) | (2R, 5S) |
| 18-6 | 3-CF3 | CH | CH | 2-Me | 5-Me | 2 | 1 | CO | 4-Py | 2-SMe | MS (FAB) m/z 450 [(M+H)+] | (2R, 5S) |
| 18-7 | 3-CF3 | CH | CH | 2-Me | 5-Me | 2 | 1 | CO | 3-Py | 6-CN | mp: 220–222(AcOEt) | (2R, 5S) |
| 18-8 | 3-CF3 | CH | CH | 2-Me | 5-Me | 2 | 1 | CO | 4-Py | 2-F | MS (FAB) m/z 422 [(M+H)+] | (2R, 5S) |
| 18-9 | 3-CF3 | CH | CH | 2-Me | 5-Me | 2 | 1 | CO | 4-Py | 2-CF3 | MS (FAB) m/z 472 [(M+H)+] | (2R, 5S) |
| 18-10 | 3-Cl | CH | CH | 2-Me | 5-Me | 2 | 1 | CO | 4-Py | — | mp: 179–184(EtOH) | trans mono-hydrochloride |
| 18-11 | 3-CF3 | CH | CH | 2-Me | 5-Me | 2 | 1 | CO | 3-Py | OCH2CF3 | MS (FAB) m/z 502 [(M+H)+] | (2R, 5S) |
| 18-12 | 3-CF3 | CH | CH | 2-Me | 5-Me | 2 | 1 | CO | 3-Py | 2-OPh | MS (FAB) m/z 496 [(M+H)+] | trans |
| 18-13 | 3-CF3 | CH | CH | 2-Me | 5-Me | 2 | 1 | CO | 4-Py | 2-tBu | mp: 175–177(AcOEt—Hex) | trans |
| 18-14 | 3-CF3 | CH | CH | 2-Me | 5-Me | 2 | 1 | CO | 3-Py | 6-SMe | MS (FAB) m/z 450 [(M+H)+] | trans |
| 18-15 | 3-CF3 | CH | CH | H | H | 2 | 1 | CO | 4-Py | 2-F | mp: >200(AcOEt) | |
| 18-16 | 3-CF3 | CH | CH | 2-Me | 5-Me | 2 | 1 | CO | 4-Py | 2-OMe | MS (FAB) m/z 434 [(M+H)+] | (2R, 5S) |
| 18-17 | 3-CF3 | CH | CH | 2-Me | 5-Me | 2 | 1 | CO | 4-Py | 2-Me | MS (FAB) m/z 418 [(M+H)+] | (2R, 5S) |
| 18-18 | 3-CF3 | CH | CH | 2-Me | 5-Me | 2 | 1 | CO | 4-Py | 2-Cl | mp: 213–215(AcOEt—Hex) | (2S, 5R) |
| 18-19 | 3-CF3 | CH | CH | 2-Me | 5-Me | 2 | 1 | CO | 4-Py | — | mp: >200(i-Pr2O) | (2S, 5R) mono-hydrochloride |
| 18-20 | 3-CF3 | CH | CH | 2-Me | 5-Me | 2 | 1 | CO | 3-Py | 5-Cl | MS (FAB) m/z 438 [(M+H)+] | (2R, 5S) |
| 18-21 | 3-CF3 | CH | CH | 2-Me | 5-Me | 2 | 1 | CO | 3-Py | 6-Me | MS (FAB) m/z 418 [(M+H)+] | (2R, 5S) |
| 18-22 | 3-CF3 | CH | CH | 2-Me | 5-Me | 2 | 1 | CO | 4-Py | 2-OCH2CF3 | MS (FAB) m/z 502 [(M+H)+] | (2R, 5S) |
| 18-23 | 3-CF3 | CH | CH | 2-Me | 5-Me | 2 | 1 | CO | 4-Py | 2,6-diMe | MS (FAB) m/z 432 [(M+H)+] | (2R, 5S) |
| 18-24 | 3-CF3 | CH | CH | 2-Me | 5-Me | 2 | 1 | CO | 4-Py | 2-i-Pr | mp: 171–174(AcOEt—Hex) | trans |
| 18-25 | 3-CF3 | CH | CH | 2-Me | 5-Me | 2 | 1 | CO | 3-Py | 2-F | MS (FAB) m/z 422 [(M+H)+] | trans |
| 18-26 | 3-CF3 | CH | CH | 2-Me | 5-Me | 2 | 1 | CO | 3-Py | 6-CO2Me | MS (FAB) m/z 462 [(M+H)+] | trans |
| 18-27 | 3-CF3 | CH | CH | 2-Me | 5-Me | 2 | 1 | CO | 3-Py | 6-NMeAc | MS (FAB) m/z 475 [(M+H)+] | trans |

TABLE 10-continued

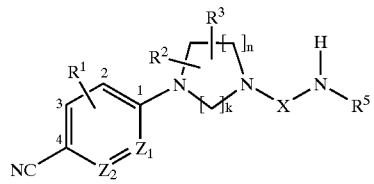

| Ex | $R^1$ | $Z_1$ | $Z_2$ | $R^2$ | $R^3$ | k | n | X | $R^5$ | Substituent on $R^5$ | DATA | Remarks |
|---|---|---|---|---|---|---|---|---|---|---|---|---|
| 18-28 | 3-CF3 | CH | CH | 2-Me | 5-Me | 2 | 1 | CO | 2-Qy | — | MS (FAB) m/z 454 [(M+H)+] | (2R, 5S) |
| 18-29 | 3-CF3 | CH | CH | 2-Me | 5-Me | 2 | 1 | CO | 4-Benzofurazanyl | — | MS (FAB) m/z 444 (M+) | (2R, 5S) |
| 19-1 | 3-CF3 | CH | CH | 2-Me | 5-Me | 2 | 1 | CO | 4-Py | 2-OMe, 6-Me | MS (FAB) m/z 448 [(M+H)+] | (2R, 5S) |
| 19-2 | 3-CF3 | CH | CH | 2-Me | 5-Me | 2 | 1 | CO | 4-Py | 2-c-Pr, 6-OMe | MS (FAB) m/z 474 [(M+H)+] | trans |
| 19-3 | 3-CF3 | CH | CH | 2-Me | 5-Me | 2 | 1 | CO | 4-Py | 2-Mor | mp: 235–247(EtOH—AcOEt) | trans monohydrochloride |
| 19-4 | 3-CF3 | CH | CH | 2-Me | 5-Me | 2 | 1 | CO | 4-Py | 2-Et, 6-OMe | MS (FAB) m/z 462 [(M+H)+] | trans |
| 19-5 | 3-CF3 | CH | CH | 2-Me | 5-Me | 2 | 1 | CO | 4-Py | 2-O-i-Pr | MS (FAB) m/z 462 [(M+H)+] | trans monohydrochloride |
| 19-6 | 3-CF3 | CH | CH | 2-Me | 5-Me | 2 | 1 | CO | 4-Py | 2-(4-Mor-(CH2)2-O)— | MS (FAB) m/z 533 [(M+H)+] | (2R, 5S) dihydrochloride |
| 20 | 3-CF3 | CH | CH | 2-Me | 5-Me | 2 | 1 | CO | 4-Py | 2-Ac | MS (FAB) m/z 446 [(M+H)+] | (2R, 5S) |
| 21 | 3-CF3 | CH | CH | 2-Me | 5-Me | 2 | 1 | CO | 4-Pm | 2-NH2 | MS (FAB) m/z 420 [(M+H)+] | (2R, 5S) |
| 22-1 | 3-CF3 | CH | CH | 2-Me | 5-Me | 2 | 1 | CO | 4-Pm | 2-NHAc | mp: 191–193(AcOEt—Hex) | trans |
| 22-2 | 3-CF3 | CH | CH | 2-Me | 5-Me | 2 | 1 | CO | 4-Pm | 2-NHSO2Me | mp: 172–174(AcOEt) | trans |
| 23-1 | 3-CF3 | CH | CH | 2-Me | 5-Me | 2 | 1 | CO | 4-Py | 2-NH2 | mp: 208–211(AcOEt—Hex) | trans |
| 23-2 | 3-CF3 | CH | CH | 2-Me | 5-Me | 2 | 1 | CO | 3-Py | 6-NH2 | MS (FAB) m/z 419 [(M+H)+] | (2R, 5S) |
| 24 | 3-CF3 | CH | CH | 2-Me | 5-Me | 2 | 1 | CO | 3-Py | 6-SO2NH2 | mp: 147–153(EtOH) | trans |
| 25 | 3-Cl | CH | CH | 2-Me | 5-Me | 2 | 1 | CO | 3-Py | 6-OMe | | trans |
| 26 | 3-Cl | CH | CH | 2-Me | 5-Me | 2 | 1 | CO | 4-Py | 2-Et | | trans |
| 27 | 3-Cl | CH | CH | 2-Me | 5-Me | 2 | 1 | CO | 4-Py | 2-F | | trans |
| 28 | 3-Cl | CH | CH | 2-Me | 5-Me | 2 | 1 | CO | 3-Py | 6-CF3 | | trans |

TABLE 10-2

| Ex. | Structure | DATA | Remarks |
|---|---|---|---|
| 1-33 | (structure) | mp: 182 (AcOEt) | trans |
| 2-10 | (structure) | MS (FAB) m/z 410 [(M+H)+] | trans monohydrochloride |
| 18-30 | (structure) | MS (FAB) m/z 483 [(M+H)+] | trans monohydrochloride |

Effects of the Invention

The compound of the invention shows strong anti-androgenic action by specifically binding to the androgen receptor. Also, this is useful as a strong anti-androgen agent, because it exerts less effects upon sex hormone levels in blood.

Accordingly, the compound of the invention is useful as a therapeutic or preventive agent for prostatic cancer, benign prostatic hyperplasia, virilism, hirsutism, baldness, acne, seborrhea and the like diseases.

Usefulness of the compound of the invention has been confirmed by the following test methods.

Evaluation of binding activity for rat androgen receptor (1) Preparation of rat prostate gland cytosol fraction The ventral prostate gland was obtained from twenty-week-old male Wistar rats 24 hours after castration. The homogenized tissue was centrifuged at 800×g for 20 minutes, the supernatant was further centrifuged at 223,000×g for 60 minutes, and the resulting supernatant was recovered to obtain cytosol fraction.

(2) Measurement of specific binding of $^3$H-mibolerone to androgen receptor from rat prostate cytosol fraction The cytosol fraction obtained in the step (1) was adjusted to a protein concentration of 1 mg/ml and used as a rat androgen receptor solution. H-Mibolerone, triamcinolone acetate and dimethyl sulfoxide (DMSO) were added to 400 μl of the rat androgen receptor solution to respective final concentrations of 1 nM, 1 μM and 5%, and the final volume was adjusted to 0.5 ml. After 18 hours of standing at 4° C., this was mixed with 500 μl of a solution containing 0.05% of Dextran-T70 and 0.5% of Dulco G-60, and the mixture was allowed to stand at 4° C. for 15 minutes and then centrifuged to recover the supernatant. A 600 μl portion of the thus recovered supernatant was mixed with 5 ml of Bioflow and then the radioactivity was measured to calculate the total amount of $^3$H-mibolerone bonded to the rat androgen receptor. The amount of non-specific binding was calculated in the same manner by adding a DMSO solution containing unlabeled mibolerone instead of the aforementioned DMSO, in such an amount that the final concentration of unlabeled mibolerone became 40 μM. The difference between the total binding amount and the non-specific binding amount was defined as the specific binding amount.

(3) Activity of the compound of the invention to inhibit specific binding of $^3$H-mibolerone Specific binding amount of $^3$H-mibolerone bound to the rat androgen receptor in the presence of the compound of the invention was calculated by adding a DMSO solution containing varied concentration of the compound of the invention, simultaneously with $^3$H-mibolerone, and carrying out the similar reaction as (2). Based on this value and the value calculated in (2), $IC_{50}$ of the inhibition activity of the compound of the invention on the specific binding of $^3$H-mibolerone was calculated. Also, dissociation constant Ki was calculated from the $IC_{50}$ value by the formula of Cheng and Prusoff*.

*: Cheng Y. C. and Prusoff W. H., Relationship between the inhibition constant (Ki) and the concentration of inhibitor which causes 50% inhibition of an enzymatic reaction., Biochem. Pharmacol., 22, 3099 (1973)

Test results of the compound of the invention are shown in the following table.

TABLE 11

| Compound | | Binding activity for rat androgen receptor (Ki = nM) |
|---|---|---|
| Example | 6-1 | 7.56 |
| | 6-13 | 3.58 |
| | 13-1 | 1.91 |
| | 18-4 | 5.01 |
| | 18-7 | 6.66 |
| | 18-8 | 15.6 |
| | 21 | 1.81 |

Based on the above test results, it was confirmed that the compound of the invention specifically binds to the androgen receptor and thereby inhibits binding of androgen and androgen receptor.

Prostate gland reducing action in mature male rat

The compound of the invention was suspended in 0.5% methyl cellulose solution and orally administered to male Wistar rat of 10 weeks of age, once a day continuously for 15 days. After 6 hours of the final administration, wet weight of the ventral prostate gland was measured to evaluate prostate gland reducing action of the compound of the invention.

The prostate gland reducing action of the compound of the invention was calculated based on the following formula, using a test group in which the compound of the invention was administered, a control group in which methyl cellulose alone was administered and a castration group in which the animal was castrated just before the administration and then methyl cellulose alone was administered.

Reducing ratio (%)=100(B−A)/(B−C)
A: Wet weight of ventral prostate gland in test group
B: Wet weight of ventral prostate gland in control group
C: Wet weight of ventral prostate gland in castration group The $ED_{50}$ value was calculated from the thus obtained reducing ratio by linear regression analysis.

Based on the above test results, the compounds shown in Table 11 showed a $ED_{50}$ value in the range of 0.3 to 11 mg/kg, which was approximately from 2 to 60 times higher activity than that of bicalutamide which has the most strongest action among currently used anti-androgen agents.

Thus, the compound of the invention has strong androgen receptor inhibition action and markedly excellent prostate gland reducing action in mature male rats and is useful as a therapeutic agent for prostatic cancer, benign prostatic hyperplasia, virilism, hirsutism, baldness, acne, seborrhea and the like diseases which are progressed by androgen.

What is claimed is:

1. A cyanophenyl compound represented by the following formula (I) or a salt thereof

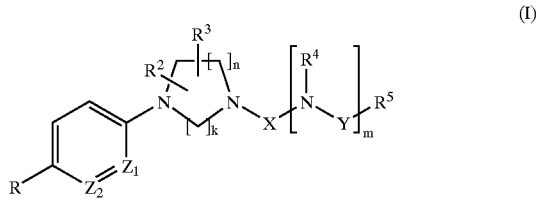

(I)

wherein each symbol has the following meaning,
R: cyano or nitro group,
$R^1$: a halogen atom or a cyano, halogeno-lower alkyl, nitro, carboxyl, lower alkyl, $R^6$—A—, $R^7$—S(O)$_p$—, lower alkyl-C(=O)— or lower alkyl-O—C(=O)— group, $R^2$ and $R^3$: these may be the same or different from one another and each means a lower alkyl group, a carbamoyl group which may be substituted by 1 or 2 lower alkyl groups, or a lower alkyl-C(=O)— or lower alkyl-O—C(=O)— group, wherein $R^2$ and $R^3$ bind to optional carbon atoms on the ring, $R^4$: this may be the same or different from one another and each means a hydrogen atom, a lower alkyl group, a carbamoyl group which may be substituted by 1 or 2 lower alkyl groups or a lower alkyl-C(=O)— or lower alkyl-O—C(=O)-group, wherein $R^2$ and $R^3$ bind to optional carbon atoms on the ring, $R^5$: a lower alkyl; aryl-lower alkyl-O—; carboxyl; lower alkyl-O—C(=O)—; amido which may be substituted by 1 or 2 lower alkyl groups; an aryl, a monocyclic or bicyclic five or six-membered heterocycle containing from 1 to 4 hetero atoms selected from nitrogen, oxygen and sulfur, or cycloalkyl group each of the aryl, heterocycle and cycloalkyl is unsubstituted or substituted with 1 to 3 substitutents each selected from the group consisting of a halogen atom, halogeno-lower alkyl, lower alkyl, lower alkyl-O—, lower alkyl-S—, lower alkyl —S(O)—, lower alkyl-S(O)$_2$—, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O—C(=O)—, aryl-O—, amino-O—, carbamoyl which may be substituted by 1 or 2 lower alkyl, or carboxyl or lower alkyl-O—C(=O)—, a monocyclic or bicyclic five or six-membered heterocycle containing from 1 to 4 hetero atoms selected from nitrogen, oxygen and sulfur, and OH group(s); or N($R^{13}$)$R^{14}$-lower alkyl-O—; with the proviso that when m=1, $R^4$ and $R^5$ may together form a five- or six-membered heterocycle which may have other hetero atoms, $R^6$: a halogeno-lower alkyl; aryl; or lower alkyl which may be substituted by N($R^9$)$R^{10}$, OH or lower alkyl-O—, $R^7$: a lower alkyl, aryl or N($R^{11}$)$R^{12}$ $R^8$, $R^9$, $R^{10}$, $R^{11}$, $R^{12}$, $R^{13}$ and $R^{14}$: hydrogen, lower alkyl or aryl, with the proviso that $R^6$ and $R^8$, $R^9$ and $R^{10}$ or $R^{13}$ and $R^{14}$ may together form a nitrogen-containing cycloalkyl which may have other hetero atoms and which is unsubstituted or substituted with 1 to 3 substituents each selected from the group consisting of a halogen atom, halogeno-lower alkyl, lower alkyl, lower alkyl-O—, lower alkyl-S—, lower alkyl-S(O)—, lower alkyl-S(O)$_2$—, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O—C(=O)—, aryl-O—, amino-O—, carbamoyl which may be substituted by 1 or 2 lower alkyl, or carboxyl or lower alkyl-O—C(=O)—, a monocyclic or bicyclic five or six-membered heterocycle containing from 1 to 4 hetero atoms selected from a nitrogen atom, an oxygen atom and sulfur atom which is unsubstituted or substituted with 1 to 2 substitutents each selected from the group consisting of an oxo group, a lower alkyl group, alkyl group, and an OH group, k: 2, n:1, m: 0 or 1, p: 0, 1 or 2, A: an oxygen atom or $NR^8$, X: —C(=O)— group, Y: a bond, lower alkylene, —C(=O)— or —S(O)$_2$— group, with the proviso that, when $R^5$ is a lower alkyl group, Y is a group other than lower alkylene, and $Z_1$ or $Z_2$: CH.

2. The cyanophenyl compound or a salt thereof according to claim 1, wherein R is a cyano group.

3. The cyanophenyl compound or a salt thereof according to claim 2, wherein $R^1$ is a halogen atom, cyano, halogeno-lower alkyl, nitro or lower alkyl-O—; $R^2$ and $R^3$: at least one of them is a lower alkyl group; $R^4$: a hydrogen atom or a lower alkyl group; $R^5$: an aryl, a monocyclic or bicyclic five- or six-membered heterocycle containing from 1 to 4 hetero atoms selected from a nitrogen atom, an oxygen atom and a sulfur atom, or cycloalkyl group, each of the aryl, heterocycle and cycloalkyl is unsubstituted or substituted with 1 to 3 substituents each selected from the group consisting of a halogen atom, halogeno-lower alkyl, lower alkyl, lower alkyl-O—, lower alkyl-S—, lower alkyl-S(=O)—, lower alkyl-S(O)$_2$—, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O—C(=O)—, aryl-O—, amino-O—, carbamoyl which may be substituted by 1 or 2 lower alkyl or carboxyl or lower alkyl-O—C(=O)—, a monocyclic or bicyclic five- or six-membered heterocycle containing from 1 to 4 hetero atoms selected from a nitrogen atom, an oxygen atom and a sulfur atom, and OH group; k is 2, n is 1; m is 1, X is C(=O)— group; Y is a bond; and $Z^1$ or $Z^2$ both means CH.

4. The cyanophenyl derivative according to claim 3, wherein the substituent group of the aryl, heterocyclic or cycloalkyl group of $R^5$ which may have a substituent group is a radical selected from the group consisting of a halogen atom, halogeno-lower alkyl, lower alkyl, lower alkyl-O—, lower alkyl-S—, lower alkyl-S(O)—, lower alkyl-S(O)$_2$—, cyclopropyl, 2-morpholin-4-yl-ethoxy, sulfamoyl which may be substituted by 1 or 2 lower alkyl groups, halogeno-lower alkyl-O—, cyano, nitro, oxo(=O), lower alkyl-C(=O)—, aryl-C(=O)—, amino which may be substituted by 1 or 2 of lower alkyl or lower alkyl-C(=O)— or lower alkyl-O—C(=O)—, aryl-O—, amino-O—, carbamoyl which may be substituted by lower alkyl, carboxyl, lower alkyl-O—C(=O)—, heterocycle, cyclopropyl and OH group(s).

5. A compound, or a salt thereof, selected from (2R,5S)-4-(4-cyano-3-trifluoromethylphenyl)-N-(6-methoxy-3-pyridyl)-2,5-dimethylpiperazine-1-carboxamide; (2R,5S)-N-(2-amino-4-pyimidin-4-yl)-4-(4-cyano-3-trifluoromethylphenyl)-2,5-dimethylpiperazine-1-carboxamide; (2R,5S)-4-(4-cyano-3-trifluoromethylphenyl)-2,5-dimethyl-N-(6-trifluoromethyl-3-pyridyl)piperazine-1-carboxamide; (2R,5S)-4-(4-cyano-3-trifluoromethylphenyl)-N-(2-fluoro-4-pyridyl)-2,5-dimethylpiperazine-1-carboxamide; 4-(4-cyano-3-trifluoromethylphenyl)-N-[2-(2-cyclopropyl-6-methoxy-4-pyridyl)-2,5-dimethylpiperazine-1-carboxamide; 4-(4-cyano-3-trifluoromethylphenyl)-2,5-dimethyl-N-[2-(2-morpholin-4-yl-ethoxy)-4-pyridyl]piperazine-1-carboxamide; and (2R,5S)-N-(2-bromo-4-pyridyl)-4-(4-cyano-3-trifluoromethylphenyl)-2,5-dimethylpiperazine-1-carboxamide.

6. A pharmaceutical composition for inhibiting binding to the androgen receptor, which comprises as an active ingredient the cyanophenyl compound of claim 1 or a pharmaceutically acceptable salt thereof in an amount sufficient for expressing an anti-androgen activity, and a pharmaceutically acceptable carrier.

7. A method for inhibiting binding to an androgen receptor, comprising administering to an animal as an active ingredient the cyanophenyl derivative of claim 1 or a pharmaceutically acceptable salt thereof in an amount sufficient for expressing an anti-androgen activity, and a pharmaceutically acceptable carrier.

* * * * *

UNITED STATES PATENT AND TRADEMARK OFFICE
CERTIFICATE OF CORRECTION

PATENT NO. : 6,673,799 B1
DATED : January 6, 2004
INVENTOR(S) : Masakazu Imamura et al.

It is certified that error appears in the above-identified patent and that said Letters Patent is hereby corrected as shown below:

<u>Column 48,</u>
Lines 53-62, delete formula (I), and insert:

-- 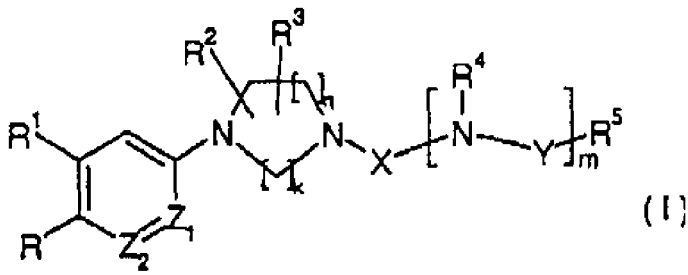 --

Signed and Sealed this

Fifteenth Day of March, 2005

JON W. DUDAS
*Director of the United States Patent and Trademark Office*